United States Patent [19]

Schreier et al.

[11] Patent Number: 4,745,074
[45] Date of Patent: May 17, 1988

[54] BLOOD-FLUID COMPOSITION FOR CELL LYSIS SYSTEM

[75] Inventors: Hans Schreier; Francis J. Martin, both of San Francisco; Viola T. Kung, Menlo Park; Francis C. Szoka, San Francisco, all of Calif.

[73] Assignee: Cooper-Lipotech Partnership, Menlo Park, Calif.

[21] Appl. No.: 583,095

[22] Filed: Feb. 23, 1984

[51] Int. Cl.$^4$ ............... G01N 33/536; G01N 33/543; G01N 33/555

[52] U.S. Cl. .................... 436/518; 436/520; 436/522; 436/536; 436/821; 436/829; 436/825

[58] Field of Search ........... 435/4, 7, 810; 436/518, 436/519, 520, 522, 536, 807, 821, 829, 10, 16, 825

[56] References Cited

U.S. PATENT DOCUMENTS

| | | | |
|---|---|---|---|
| 4,429,008 | 1/1984 | Martin et al. | 436/829 |
| 4,483,921 | 11/1984 | Cole | 435/810 |
| 4,483,929 | 11/1984 | Szoka | 436/829 |
| 4,590,169 | 5/1986 | Cragle et al. | 436/829 |
| 4,636,479 | 1/1987 | Martin et al. | 436/829 |

OTHER PUBLICATIONS

Mold et al., J. Immunol., 125(2):696–700 (1980).
Uemura et al., J. Immunol., Methods, 53:221–232 (1982).
Mattiasson et al., in *Enzyme—Immunoassay*, Maggio (Ed.), CRC Press, Inc., Boca Raton, Fla., 232 (1980).
Szoka et al., Proc. Nat'l. Acad. Sci. USA 75(9):4194–4198 (1978).
Benjamin Geiger, et al., Immunochemical Determination of Ganglioside GM2, by Inhibition of Complement-Dependent Liposome Lysis, Journal of Immunological Methods, 17 (1977) 7–19, Elsevier/North-Holland Biomedical Press pp. 7–19.

*Primary Examiner*—Esther M. Kepplinger
*Attorney, Agent, or Firm*—Ciotti & Murashige, Irell & Manella

[57] ABSTRACT

A blood fluid composition for use in a complement-mediated cell lysis system. The composition includes a blood fluid, which may be either a serum source of complement, analyte-containing serum, or both, and lipid vesicles capable of reducing the extent of non-specific cell lysis produced when the blood fluid is added to lysable target cells in the system. The vesicles are present in an amount which increases the ratio of ligand-specific to non-specific cell lysis in the system at least 2-fold and preferably 4-fold or more over that achievable in the system in the absence of the vesicles.

11 Claims, No Drawings

BLOOD-FLUID COMPOSITION FOR CELL LYSIS SYSTEM

BACKGROUND AND SUMMARY

The present invention relates to a blood-fluid composition, particularly, to a blood-fluid composition for use in a complement-mediated cell lysis system.

The following references are referred to by corresponding number herein:

1. Muller-Eberhard, H. J., Complement, *Ann. Rev. Biochem.*, 44:697 (1975).
2. Kataoka, T., Williamson, J. R., and Kinsky, S. C., *Biochem. et Biophys. Acta,* 298:158 (1973).
3. Six, H. R., Uemura, K., and Kinsky, S. C., *Biochemistry,* 12(20):4003 (1973).
4. Okada, N., Yasuda, T., Tsumita, T., and Okada, H., *Immunology,* 45:115 (1982).
5. Yasuda, T., Naito, Y., Tsumita, T., and Tadakuma, T., *J. Immonol. Methods,* 44:153 (1981).
6. Geiger, B., and Smolarsky, M., *J. Immunol. Methods,* 17:7 (1977).
7. Uemura, K., Hattori, H., Kitazawa, N., and Taketomi, T., *J. Immunol. Methods,* 53:221 (1982).
8. Stroud, R. M., Volanakis, J. E., and Lint, T. F., In: *Immunochemistry of Proteins,* edited by Atazzi, M. Z., Vol. 3, Plenum Press, N.Y., N.Y. (1979).
9. Whicher, J. T., *Clin. Chem.,* 24(1):7 (1978).
10. Szoka, F., Jr., and Papahadjopoulos, D., *Ann. Rev. Biophys. Bioeng.,* 9:467 (1980).
11. Szoka, F., Jr. and Papahadjopoulos, D., *Proc. Nat. Acad. Sci. U.S.A.,* 75:4194–4198 (1978).
12. Heath, T. D., Macher, B. A. and Papanadjopoulos, D., *Biochimica et Biophysica Acta,* 640:66–81 (1981).
13. Martin, F. J., Hubbell, W. L., and Papahadjopoulos, D., *Biochemistry,* 20:4229–4238 (1981).
14. Martin, F. J. and Papahadjopoulos, D., *J. Biol. Chem.,* 257:286–288 (1982).
15. Bodmer, W. F., *Tissue Antigens,* 17:9 (1981).

The ability of complement to lyse lipid bilayer cells, such as red blood cells (reference 1) and liposomes (reference 2–4), in the presence of ligand-specific cell surface binding agents has been exploited in immunoassay methods for determination of ligand or anti-ligand analytes. U.S. Pat. No. 4,130,634 to Molinaro, et al. describes a method for detecting erythrocyte-specific antigens by coating the erythrocytes with anti-antigen antibody in the presence of complement, and measuring the release of hemoglobin from the lysed cells. Yasuda, et al. have described a simple method for measuring anti-glycolipid antibody by reacting the antibody with complement and liposomes containing surface glycolipid, where cell lysis and release of a fluorogenic reporter from the liposomes produces increased fluorescence in the assay medium (reference 5). Similar types of liposome immunoassays applicable to ganglioside GM$_2$ antigen (reference 6), and to Forsmann and blood group A-active gangliolipids (reference 7) have been reported.

Several types of reporters, in addition to chromophores, such as hemoglobin, and fluorogenic compounds, have been used to indicate cell lysis in immunoassays of this type. U.S. Pat. No. 3,887,698 to McConnell, et al. discloses a liposome immunoassay test system in which the difference in electron paramagnetic resonance spectra between encapsulated and released nitroxide reporter provides a measure of complement-mediated liposome lysis. U.S. Pat. Nos. 4,235,792 to Hsia, et al. and 4,342,826 to Cole disclose liposome immunoassay systems in which complement-mediated cell lysis is evidenced by the expression of liposome-encapsulated enzymes.

Immunoassay systems involving lysable lipid membrane vesicles provide important potential advantages in diagnostic test systems. One advantage is that the ligand/anti-ligand binding reaction and the measurement of released reporter from lysed cells can be performed in the same assay mixture. This single-mixture assay, which is generally referred to as a homogeneous assay, contrasts with more widely used enzyme or fluorescent immunoassays which require the steps of (1) binding a ligand-reporter complex to a solid surface in the presence of analyte in one mixture, (2) removing unbound ligand-reporter complex, and (3) measuring bound or unbound reporter levels in a second mixture. Homogeneous cell-lysis immunoassays also have the potential for high assay sensitivity, since relatively few ligand/anti-ligand binding events on the cell surface can lead to the release or expression of a large number of reporter molecules.

Heretofore, however, the reliability and sensitivity of homogeneous immunoassays have been seriously limited by variable, and in many cases prohibitively high, non-specific lysis which occurs when lysable target cells are mixed with a serum source of complement and/or a serum source of analyte. Studies conducted in support of the present application, reported below, show that serum added to a cell lysis system causes non-specific cell lysis to levels as high as 50%-70% of total releasable marker. The degree of non-specific lysis can depend on several variables, including the age, source and storage conditions of the serum, the age, lipid composition and storage conditions of the lysable target cells, and the relative concentrations of serum and lysable cells.

The causative serum factors which produce non-specific cell lysis likely include cross reactive serum antibodies, such as immunoglobulin G (IgG) and immunoglobulin M (IgM) antibodies capable of cross-reacting with cell-surface ligands to activate the classical complement pathway. It is also known that certain lipids, polynucleotides, C-reactive proteins and some viruses can stimulate the classical complement pathway. Another source of interfering factor in serum may include serum components such as polysaccharides, lipopolysaccharides and immunoglobulins which are capable of activating the alternative complement pathway. (References 1, 8 and 9 provide excellent reviews of the complement system). That one or both complement pathways are responsible for some observed non-specific lysis is supported by experiments conducted in conjunction with the present application showing that inactivation of complement components, either upon short-term storage or by heat-treating the serum, results in an appreciable decrease in the level of non-specific cell lysis. The just mentioned experiments also indicate that heat-treated serum retains substantial non-specific cell lytic activity, indicating that the serum contains yet a third type of interference factor which is distinguished by its ability to induce cell lysis via non-complement mechanism(s). It is noted that even if heat-treating serum could effectively eliminate non-specific cell-lysis, the requirement for active complement in a homogeneous assay system would preclude this approach.

It is one general object of the invention to provide a blood composition which substantially overcomes problems in variability and high non-specific lysis associated with complement-mediated cell lysis systems known in the prior art.

Another object of the invention is to provide such a composition for use in a homogeneous assay which is based on ligand-specific, complement-mediated cell lysis.

A related object of the invention is to provide, for use in such an assay system, a blood-fluid composition which substantially enhances the reliability of the assay, and increases the signal-to-noise ratio thereof generally between about 4- and 10-fold.

It is yet another object of the invention to provide such a composition which is easily and inexpensively prepared as part of a homogeneous cell lysis immunoassay.

A further object of the invention is to provide an improved complement preparation for use in a ligand-specific, complement-mediated cell lysis system.

Other objects of the invention include providing a homogeneous assay system and specific homogeneous assay kits utilizing such blood fluid composition, and providing a method for treating blood fluid to reduce non-specific lysis in a complement-mediated cell-lysis system.

The present invention includes a blood fluid composition adapted to be added to a complement-mediated cell-lysis system. The composition includes the blood fluid and lipid vesicles which, when added to the system, are capable of increasing the ratio of ligand-specific cell lysis occurring in the presence of an added anti-ligand, to non-specific lysis, occurring in the absence of added anti-ligand. The vesicles are added to the blood fluid in an amount which produces at least a 2-fold increase in the specific to non-specific ratio over that achievable in the system under the same conditions in the absence of the vesicles. In a preferred embodiment of the invention, the vesicles include liposomes predominantly in the 0.02 to 0.2 micron size range, and the vesicles are added in an amount which enhances such ratio between about 4- and 10-fold.

According to one aspect of the invention, the blood fluid composition forms part of a homogeneous assay system for the determination of ligand-related analyte, and in particular, an analyte present in a serum or plasma sample. Here the blood fluid may include both a serum source of complement and the analyte-containing serum sample. The lipid vesicles added to the system are effective in reducing non-specific lysis due to both serum sources.

A kit for the determination of a ligand-related analyte includes lysable cells, a serum source of complement, and such lipid vesicles. Also dislcosed is a method for treating blood fluid, such as serum or plasma, to reduce significantly the extent of non-specific lysis produced when the blood fluid is added to a cell-lysis system containing lysable cells.

These and other objects and features of the present invention will become more fully apparent from the following detailed description of the invention.

DETAILED DESCRIPTION OF THE INVENTION

The blood fluid composition of the present invention is intended for use in a cell lysis system containing lysable target cells. One major application of the composition is for use in a homogeneous immunoassay system, in which the target cells include unilamellar or multilamellar liposomes encapsulating a reporter which is detectable upon cell lysis. Section I below outlines methods for making target-cell liposomes of this type.

The composition of the invention generally comprises a blood fluid, such as blood serum or plasma, which may include either a serum source of complement or a analyte-containing serum or plasma sample, or both. The blood fluid is mixed with lipid vesicles whose lipid composition preferably has certain lipid components in common with the target cells, and which are also preferably small unilamellar vesicles in the 0.02 to 0.2 micron size range. Section II considers several methods of preparing lipid vesicles having size, charge and lipid and ligand composition features compatible with the present invention.

An important embodiment of the present invention is an improved complement preparation containing a serum source of complement mixed with lipid vesicles of the type described above. Section III describes methods of forming and using the complement preparation. Section IV discusses the components and precedures of the homogeneous assay system of the invention.

I. Preparing Lysable Target Cells

Lysable target cells for use in the cell lysis system of the invention are lipid bilayer cells, each encapsulating an aqueous space containing a reporter which is detectable upon cell lysis. The outer bilayer membrane carries surface-bound ligand molecules which are capable of binding specifically and with high affinity to anti-ligand molecules, to form a recognition unit capable of activating the classical complement pathway, leading to cell lysis. The cells may be either unilamellar or multilamellar liposomes whose properties and methods of preparation will be detailed below. Biological cells, such as erythrocytes, containing endogenous reporter, such as hemoglobin or cell-specific enzymes, or biological cell ghosts, such as erythrocyte ghosts which have been prepared to contain an endogenous or exogenous reporter, may also be suitable.

Properties of and methods for preparing both unilamellar and multilamellar liposomes have been detailed in the literature. The reader is referred particularly to references 10 and 11, and references cited therein, for a comprehensive discussion of the topic. Above-cited references 2–7 relating to complement-mediated liposome lysis also provide detailed information on the preparation of specific types of liposome target cells. What will be described herein are preferred methods of preparing liposomes, and particularly large unilamellar and multilamellar liposomes, and liposome properties which contribute to advantages in the invention.

Liposomes are prepared from lipid mixtures which typically include phospholipids and sterols. A list of phospholipids used commonly in liposome preparations is given on page 471 of reference 10. General considerations which determine the choice of lipids are: (1) the desired degree of fluid mobility and lipid packing density, (2) desired surface charge density and (3) the concentration of surface ligands to be attached to the cells. Fluid mobility characteristics can be important in complement-mediated lysis involving factors such as IgG, in which complement activation requires interaction of complement recognition components simultaneously with many surface bound antibodies. Packing density characteristics can be important to the success of coupling reactions used to attach ligand molecules covalently to the liposome surfaces. For example, it has been found that the inclusion of at least about 10 mole percent of cholesterol is important for the success of certain protein-coupling reactions which will be referenced below. The fluidity and packing characteristics also affect the number of bilayers in the vesicles produced and vesicle size as discussed in reference 10.

A typical lipid composition used in preparing target-cell liposomes includes between about 10% and 50% cholesterol or other sterol and between about 0.5 and 10 mole percent of the lipid to which the ligand molecules of the target cells can be individually coupled, or which themselves constitute the ligand in the target cell. The remainder lipid can include neutral phospholipids, such as phosphatidylcholine (PC) or a phospholipid mixture. Charged lipids such as phosphatidylglycerol (PG), phosphatidylserine (PS), phosphatidic acid (PA), glycolipids and charged cholesterol derivatives such as cholesterol phosphate or cholesterol sulfate may be included to produce a desired surface charge on the target cell surface. As will be appreciated from references 5–7 as well as from the present discussion, suitable target-cell liposomes can be formed from a wide variety of lipid compositions. Nonetheless, some target-cell liposomes, particularly those containing high molar concentrations of negatively charged lipids, such as lipid composition-15 described in Example VII below, show very poor susceptibility to ligand-specific lysis and are therefore unsuitable for use in the present invention. Example I below describes the preparation of the number of typical target cell liposomes, each of which is composed of between about 40 and 50 mole percent PC, 10 mole percent PG, between about 30 and 40 mole percent cholesterol and, 5 mole percent of phosphatidylethanolamine (PE) or derivatives thereof.

Multilamellar target-cell liposomes—that is, liposomes composed of a series of concentric bilayer lamellae—are prepared typically by drying a mixture of lipids in a thin film and hydrating the lipids with an aqueous buffer containing a desired concentration of soluble reporter. The size and number of lamellae in the formed lipid vesicles can be controlled, within limits, by varying the hydration time and amount of agitation used in hydrating the lipids. Vigorous agitation, brief sonication, and/or extrusion through polycarbonate membranes can be employed to obtain smaller or more uniformly sized multilamellar vesicles. It is generally desirable to produce target cell liposomes which are fairly homogeneous in size, typically between about 0.2 and 2 microns in diameter. To this end, it is advantageous to prepare a heterogeneous population of relatively large multilamellar liposomes and subsequently pass these through a polycarbonate membrane having a desired pore size to obtain the desired size distribution of liposomes. Encapsulation efficiencies of the reporter are typically between about 10% and 30%.

Multilamellar target-cell liposomes may be advantageous under conditions where cell leakage during storage or handling leads to relatively high background levels of released reporter. However, multilamellar target-cell liposomes are generally less sensitive to complement-mediated lysis than unilamellar vesicles, since reporter release requires more extensive membrane lysis and therefore, more ligand-related analyte and more complement. For this reason, unilamellar target-cell liposomes may be preferred. In one method of preparing large unilamellar vesicles, referred to as reverse phase evaporation, a desired composition of lipids is dissolved in a suitable organic solvent such as diethyl ether, isopropyl ether, or a solvent mixture such as isopropyl ether in chloroform (1:1). An aqueous solution of soluble reporter and, optionally, a solute which contributes to a desired osmolarity in the target cell, is added directly to between about three and six volumes of the lipid solvent mixture. The preparation is sonicated for a brief period to form a homogeneous water-in-oil (W/O) emulsion. The organic solvent, or solvent mixture is then removed under reduced pressure, resulting in the formation of a viscous, gel-like intermediate phase which spontaneously forms a vesicle dispersion when residual solvent is removed by evaporation under reduced pressure. The resulting vesicles, referred to as reverse-phase evaporation vesicles or REV's, are predominantly unilamellar vesicles in the size range between about 0.5 and 10 microns. The liposome suspension can be passed through a micropore filter of defined pore size, as described above, to achieve a more homogeneous size range of liposomes. Non-encapsulated reporter molecules can be removed readily by one or more centrifugation wash steps. Example I below details a specific method for forming REV's having one of a number of different lipid compositions. The reader is referred to references 10 and 11 for further details of the reverse phase evaporation technique, as well as alternative methods for forming unilamellar vesicles.

One advantage of the reverse phase evaporation technique is that it may be used to encapsulate water-soluble molecules sufficiently within the interior of the liposome spaces. This feature is particularly advantageous in the present invention where it is desired to encapsulate a water-soluble reporter efficiently. Alternative methods may be more advantageous, however, where the encapsulated reporter is an enzyme or other biomolecule which is susceptible to denaturation upon exposure to organic solvents.

The encapsulated reporter is preferably one whose release from lysed target cells can be detected in a suspension of the cells. Such reporters include fluorogenic compounds which are highly quenched at the relatively high reporter compositions within encapsulated liposomes, and stable free radical compounds, such as nitroxide spin labels, whose spin coupling characteristics are highly concentration dependent. Exemplary fluorogenic compounds include 6-carboxyfluorescein (CF), 4-methylumbelliferyl phosphate and 1-aminonaphthalane-3,6,8-trisulfonate (ANTS). Exemplary stable free radicals include water-soluble nitroxide free radicals, such as those described in above mentioned U.S. Pat. No. 3,887,698.

Enzyme reporters are preferably those whose activity can be measured readily by spectrophotometric methods. Representative classes of enzymes contemplated herein include oxidoreductases, typified by glucose oxidase, galactose oxidase and catalase; hydrolases, typified by various phosphatases, such as alkaline phosphatase; glycoside hydrolases, such as beta-galactosidase; peptidases; and lipases.

The ligand molecules carried on the target cell surfaces are adapted to bind specifically and with high affinity to an anti-ligand in the immunoassay reaction medium, to activate complement lysis of the target cells. A number of ligand/anti-ligand binding complexes which activate the complement are listed in TABLE II of reference 9, and include antibody/antigen complexes of IgM, $IgG_1$ and $IgG_3$, which bind strongly to the complement activating unit, and IgG$_2$ which binds weakly to the unit, Staphyloccal protein A/IgG complex, and bovine conglutinin/conglutinogen complex. The ligand, as defined herein, may be either member of the activating complex, e.g., either the antigen or antibody of the IgG complex, the anti-ligand being the other member of the pair. As will be seen below, the analyte to be determined in a liposome immunoassay of the invention may be an anti-ligand capable of binding specifically to ligand molecules on the cell surface, a ligand or ligand-like compound capable of competing with an anti-ligand for binding to the cell surface ligand, or the ligand itself, where the immunoassay system includes target cell analyte-binding molecules capable of binding the analyte to the cells, and anti-ligand molecules capable of binding to the surface-bound ligand.

Several methods are available for forming surface arrays of ligand or ligand-binding molecules on target-cell liposomes. Where the ligand is a lipid antigen, such as group A-active glycolipids, cardiolipin, or a ganglioside, the lipid antigen may be added directly to the lipid components used in forming the liposomes. Water soluble antigens which are first covalently coupled to lipid component molecules such as phospholipid molecules can also be incorporated directly into the lipids used in forming the liposomes. Chemical reaction methods for attaching various reactive groups in antigens to polar groups in lipids are well known to those skilled in the art. Example I below describes liposomes having a surface array of dinitrophenyl phosphate (DNP) formed by inclusion of DNP-PE into the liposome lipids.

Many ligands, particularly higher molecular-weight biopolymers, such as proteins and nucleic acids, are preferably coupled to polar, reactive head groups of lipids in already-formed liposomes. Several types of reactions for coupling ligand molecules covalently to lipid head groups are known; of these, the methods described in references 12–14 below have been used to attach relatively high surface concentrations of proteins to liposome surfaces. The reader is also referred to patent applications for "Lipid-Vesicle-Surface Assay Reagent", Ser. No. 452,798, filed Dec. 23, 1982, "Enhanced Agglutination Method and Kit", Ser. No. 486,793, filed Apr. 20, 1983, and "Large Liposome Agglutination Test", Ser. No. 517,826, filed July 27, 1983, all assigned to the assignee of the present application, for detailed procedures used in coupling antibodies and antibody fragments to liposome surfaces. Most of the specific ligand/anti-ligand pairs described in these applications are suitable for use in the present invention.

The surface concentration of ligand molecules is one selected to ensure that a substantial level of target-cell lysis will be produced in the presence of anti-ligand. The surface concentration will depend in part on the number of ligand/anti-ligand complexes required to activate complement-mediated lysis. It is known, for example, that a single antibody/antigen IgM complex can trigger the classical complement pathway, whereas several, and perhaps as many as 1,000, antibody/antigen IgG complexes are required for complement activation. In the ligand-coated REV target cell liposomes described in Example I, the concentration of the DNP antigen is about 5 mole percent of the total lipid bilayer components of the target cell. Protein coupling ratios of between about 300–600 micrograms protein per micromole vesicle lipid may be achieved by known procedures, such as those referenced above.

As indicated, biological cells, such as blood cells, may be suitable as target cells in the immunoassay system of the invention. Here, the encapsulated reporter is preferably an endogenous molecule, such as hemoglobin or a cell-specific enzyme whose activity can provide a measure of cell lysis. The surface ligand may be either an endogenous surface antigen, or may be an exogenous ligand which is attached to the cell by methods similar to those applicable to liposomes. Example VII below describes a cell immunoassay system in which the presence of cell-specific erythrocyte antigens is determined by release of hemoglobin from sheep erythrocytes.

II. Preparing Lipid Vesicles

According to an important feature of the present invention, the extent of non-specific lysis which is normally produced when blood fluid, such as serum or plasma, is added to lysable target cells in the presence of complement, is inhibited several-fold by the presence of lipid vesicles of a type detailed herein. Where the target cells include liposomes, as described in Section I, the lipid vesicles preferably include liposome vesicles. Where the target cells are biological cells, such as red blood cells, the vesicles preferably include ghosts of the corresponding cell or of a related cell, or liposomes having an outer membrane composition similar to that of the cells.

Liposomal vesicles are prepared from lipid mixtures such as those already described in Section I. The choice of phospholipid will depend in part on the lipid composition of the associated target-cell liposome. As a general guideline, the lipid vesicles should contain, as a major phospholipid (defined herein as one which comprises at least about 10 mole percent of the liposome lipid components), at least one of the major phospholipids making up the target-cell liposomes. As will be seen in Example V below, target-cell liposomes containing between about 40% and 50% PC show substantially reduced non-specific lysis in the presence of lipid vesicles containing between about 35% and 100% PC. The compatibility of lipid components in the target-cell liposomes and lipid vesicles may be more crucial for certain phospholipids, particularly phosphatidylethanolamine and derivatives thereof. The studies reported in Examples XIII and XIV, for example, indicate that where the target vessels contain PE-coupled antigen, substantially greater inhibition of serum-related non-specific inhibition is achieved by adding lipid vesicles which also contain derivatized PE. This is true even though the molar amounts of PE derivatives in the target cell and lipid vesicles are only about 5 mole percent or less.

No specific requirement for a sterol, such as cholesterol, was established in studies conducted in support of the present application. It will be seen particularly in Example V below that SUV's containing either 100 mole percent PC, 70 mole percent PC plus 30 mole percent cholesterol or mixtures of PC, cholesterol and other lipids each inhibited non-specific target cell lysis to about the same degree.

Similarly, no requirement for charged lipids was observed. (The above-mentioned effect of PE or derivatives thereof appears to be related to this lipid class specifically, rather than to the presence of a positively charged head group, since uncharged PE derivatives show substantially the same effect.) Certain negatively charged lipids, such as PG, are shown herein to inhibit ligand-specific target-cell lysis dramatically when present in vesicles at a molar concentration of about 10% or more. However, other studies suggest that the effect of PG-containing lipid vesicles on the inhibition of specific target cell lysis is not attributable to the lipid's negative charge per se. As will be seen in Example V, lipid vesicles containing 30 mole percent PG plus 5 mole percent of derivatized PE showed no inhibition of ligand-specific target-cell lysis. Further, lipid vesicles whose composition is substantially like that of erythrocyte ghosts, and which therefore include about 35 mole percent of the negatively charged lipid phosphatidylserine (PS), showed no inhibitory effect on ligand-specific target cell lysis (Example VII).

The lipid vesicles may also be formed to include surface-bound ligand molecules or ligand-like molecules capable of competing with the target-cell ligands for binding to anti-ligand. Experimental data reported herein suggest that ligands bound to lipid vesicles may act to reduce non-specific target cell lysis by binding serum molecules capable of cross-reacting with target cell ligands. High concentrations of lipid vesicle ligand, due to high ligand surface concentrations on the vesicles and/or high vesicle concentrations, should be avoided however, since the ligands can inhibit ligand-specific cell lysis by competing with target cell ligands for binding to anti-ligand. Example XVI below demonstrates that at a lipid vesicle ligand concentration comparable to that of target cell ligand, marked inhibition of specific target cell lysis is observed.

Methods for preparing larger-size multilamellar and unilamellar vesicles have been described above in Section I. While larger lipid vesicles are effective in reducing non-specific lysis of target cells in the presence of added serum, an important finding herein is that small unilamellar vesicles (SUV's), predominantly in the 0.02 to 0.05 micron size range, reduce non-specific lysis up to about 8 times more efficiently, in terms of lipid vesicle concentration required to achieve a desired inhibition level. Methods for forming SUV's have been reviewed in reference 10. According to one widely used procedure, SUV's are produced by sonicating a dispersion of MLV's to optical clarity, resulting in a suspension of unilamellar vesicles having diameters of about 0.2 microns or less. The sonication is typically carried out with a bath type sonicator or probe sonicator under an inert atmosphere for between about 10 and 45 minutes, depending on sonication power.

In another technique, liposomes are formed by removal of detergent, such as cholate or deoxycholate, from a detergent-phospholipid mixture. Removal of the detergent by centrifugation, gel-filtration, or fast-control dialysis leads to the formation of a homogeneous population of unilamellar vesicles with mean diameters of about 0.08–0.2 microns. An alternate method that avoids both sonication and detergent is an ethanol injection technique in which lipids dissolved in ethanol are rapidly injected into a buffer solution where they spontaneously form small unilamellar vesicles (reference 10).

Where the lipid vesicles are prepared to include surface bound ligands, the techniques described in Section I for introducing bound antigens or large biological molecules such as proteins to lipid vesicle surfaces may be used. Example II below describes the preparation of SUV's suspensions by the above-described sonication tecnique. Two of the suspensions contain dinitrophenyl phosphate (DNP) ligand incorporated into the SUV's by including DNP-derivatized PE in the lipid composition used in forming the vesicles.

As suggested above, lipid vesicles intended for use in a cell lysis system containing biological target cells may require a more complex lipid and protein composition, preferably one which is substantially like that of the biological membrane target cell. Example VII below examines the inhibition of non-specific erythrocyte cell lysis by (1) SUV's containing a PC, PG, cholesterol mixture, (2) SUV's whose lipid composition is substantially like that of erythrocyte membranes, and (3) erythrocyte ghosts. Of these three types of lipid vesicles, only the erythrocyte ghosts were effective in reducing non-specific erythrocyte lysis. Thus, for more complex target cells, such as biological cells, there appears to be a requirement for protein compatibility between the lipid vesicles and the target cells. Biological cells ghosts, such as erythrocyte ghosts, can be prepared from one of a number of known methods. In a preferred method, used in Example VII, washed erythrocytes were subjected to rapid osmotic shock in cold hypotonic medium and reannealed by heating in isotonic saline at 37° C. Slow dialysis of the cells against hypotonic solution or drug-induced cell lysis or other methods which may be suitable.

The above discussion is summarized in the following guidelines for preparing lipid vesicles capable of enhancing the ratio of ligand-specific to non-specific, complement-mediated lysis of selected target cells:

1. In the case of liposomal target cell, a wide latitude in lipid composition is permitted, although a composition which closely resembles that of the target cell lipid composition may be preferred;

2. Where the target cell includes PE or derivatized PE, the lipid vesicles should also contain PE or a PE derivative;

3. Charged phospholipids, such as PG, which are found to inhibit ligand-specific lysis of liposomal target cells, should be omitted or included at a reduced molar concentration in the vesicles;

4. The vesicles may be advantageously prepared to include surface-bound ligand molecules, at a combined surface and vesicle concentrations which does not inhibit ligand-specific target cell lysis;

5. SUV's are much more efficient in inhibiting non-specific lysis of liposomal target cell than larger multilamellar or unilamellar vesicles; and 6. Preferred lipid vesicles for use with biological target cells may require a complex lipid and protein composition which resembles, or is substantially identical to that of the target cells.

III. Improved Complement Preparation

An improved complement preparation formed in accordance with the present invention includes a serum source of complement and lipid vesicles of the type described above. The complement is intended for use in producing ligand-specific cell lysis in a complement-mediated cell lysis system characterized by both non-specific and ligand-specific cell lysis in the presence of serum. The lipid vesicles are adapted, when added to the system, to increase the ratio of ligand-specific to non-specific cell lysis at least about 2-fold over that achievable in the system, under the same conditions, in the absence of added vesicles.

The serum source of complement includes a blood fluid, preferably serum or plasma, containing the serum complement components required to mediate complement lysis, either by the classical or alternative complement pathways. The serum source may be essentially unfractionated serum or plasma, or may be a blood fluid which has been partially purified to enrich the fluid in one or more complement components. Typically, the serum source includes rabbit or guinea pig serum which can be obtained from commercial sources, and is usually supplied in the form of a lyophilized serum powder and a reconstitution solution. Example III describes complement preparations containing reconstituted guinea pig serum obtained from three different commercial sources.

The lipid vesicles are added to the serum complement source, or to a cell lysis system containing the serum source, in an amount which increases the ligand-specific to non-specific ratio at least about 2-fold over that achievable, under comparable conditions, in the absence of added vesicles. Preferably, the vesicles are added in an amount which increases such specific to non-specific ratio more than 4-fold, as demonstrated in several of the examples. The quantity of vesicles added to the complement source, or to the system containing the complement source, to achieve the desired increase in specific to non-specific ratio, can vary with both the composition and size of the lipid vesicles, and with the relative concentrations of complement and lipid vesicles. The effect of lipid composition and size has been discussed in Section II, and in studies discussed in Example XVIII below, which show that SUV's are about 8 times more efficient than either MLV's or REV's in reduced serum-related non-specific lysis of target cells in the presence of complement.

The effect of the relative concentrations of complement and SUV's is explored in Example VI. As will be seen, there is a substantial, systematic reduction in the extent of non-specific target cell lysis when either the concentration of complement in the target cell system is reduced, or the concentration of SUV's added to the system is increased.

An experiment designed to study the non-specific lytic activity of the complement preparation as a function of relative SUV and target-cell REV concentrations was also performed. Briefly, it was found that at each selected REV concentration, there was observed a decrease in non-specific lysis as the concentration of SUV's added to the complement was increased, similar to that reported in TABLE VI. However, at fixed SUV and complement concentrations, there was no significant change in the extent of non-specific lysis over a 10-fold concentration range of target-cell REV's in the system. Thus the relative concentrations of SUV's and REV's in the cell system does not appear to be critical.

A method of treating serum complement by exposing the serum to lipid vesicles, and removing the vesicles before adding the serum to a cell lysis system was also investigated. As detailed in Example VIII, a suspension of MLV's was added to guinea pig complement serum, the mixture incubated, and the MLV's removed from the complement by centrifugation. (Treatment with MLV's, rather than SUV's was studied, because of the ease with which MLV's could be removed from treated serum by centrifugation.) The vesicle-treated complement was compared to an REV target-cell lysis system with untreated guinea pig serum and with a complement preparation containing guinea pig serum and added MLV's. The results of the study show that the vesicle-treated serum source (with MLV's removed) increased the specific to non-specific lysis ratio produced in the presence of the complement over that of serum complement alone, but that the complement preparation prepared by including MLV's in the cell lysis system produced a substantially greater increase in the ratio of specific to non-specific cell lysis. The results indicate that the continued presence of the added lipid vesicles is required in order to achieve optimal inhibition of non-specific lysis.

A method of treating serum complement to remove immunoglobulin G molecules from a serum source of complement was also investigated. Sepharose TM 4B and Sepharose TM 4B having linked protein A (capable of binding IgG molecules specifically) were obtained from Bethesda Research Labs, (Gaithersburg, MD). Sepharose 4B column chromatography was carried out in phosphate buffer, pH 7.0, according to conventional procedures. Undiluted guinea pig serum was passed through one of the two Sepharose TM column, concentrated to its original volume, and tested for levels of specific and non-specific cell lysis in a cell-lysis system containing target-cell REV's. The serum which had been passed through the Sepharose column containing attached protein A gave a level of non-specific cell lysis which was about 40% less than that of untreated serum, and substantially full ligand-specific lysis. A second passage of the treated serum through the Sepharose-protein A column produced little reduction in non-specific lysis, but substantially eliminated ligand-specific lysis activity. Complement which had been passed through the column containing Sepharose 4B only showed about a 20% reduction in non-specific lysis and no appreciable change in the level of specific lysis.

The above data indicate that Sepharose 4B, and to a greater extent Sepharose 4B conjugated to protein A, were effective in removing minor portions of the interfering components present in serum which contribute to non-specific complement-mediated lysis. One role of lipid vesicles in the complement preparation of the invention, therefore, may be to sequester serum antibodies which would otherwise be free to cross-react with target cell ligand molecules. As discussed in Section II, and demonstrated in Example XIV, and in other examples, lipid vesicles containing surface-bound ligand may be more effective than non-ligand containing vesicles in reducing non-specific cell lysis, further supporting the antibody-absorption notion.

The complement preparation of the invention can be prepared as a serum/lipid vesicle mixture which is stable, as an aqueous solution, for a period of several days, or which may be stored over extended periods by freezing or lyophilization. Stability studies reported in Example X show that a complement preparation formed by adding SUV's to freshly reconstituted complement serum retains its ligand-specific and non-specific lytic characteristics in a cell lysis system for periods of up to one week when stored at refrigerator temperature. The stability of the preparation is enhanced at greater complement concentrations, and also may be more stable when stored in a polypropylene or other suitable plastic storage container, than when stored in a glass container. Example IX examines the stability of a lyophilized serum/SUV complement preparation at various storage temperatures. It was found that the lyophilized preparation is stable for up to a month when stored at $-70°$ C., for up to about two weeks at $4°$ C., and for about three days when stored at room temperature. Where long-term storage of the complement preparation is required, it is most convenient to store the serum and vesicle components of the preparation individually, and mix the two shortly before their addition to a cell lysis system or add the two individually to a cell lysis system. Both lyophilized serum and a suspension of lipid vesicles have shelf lives of up to six months or more when stored individually.

Various advantages of the complement preparation can be appreciated from the above. The improved complement preparation, when used in a cell lysis system, is effective in increasing the signal-to-noise ratio, as reflected in the increase in ligand-specific to non-specific target cell lysis, at least 2-fold, more typically 4-fold and in many cases more than 10-fold over that achievable in a system employing serum complement alone. The increase in signal-to-noise ratio is achieved typically by a several-fold reduction in the level of non-specific lysis, with the level of ligand-specific lysis being unaffected or only very slightly inhibited. The inhibition of non-specific lysis improves both the reliability and sensitivity of homogeneous liposome immunoassays used for the determination of ligand-related analytes. This feature will discussed in detail in Section IV below.

The improved preparation can also be used advantageously in complement-mediated cell lysis systems which include biological target cells. From Example VII, it will be seen that the ratio of specific to non-specific erythrocyte lysis, in the presence of an anti-ligand capable of binding specifically to cell surface antigen, can be enhanced several-fold with the complement preparation of the invention, providing a substantially improved erythrocyte typing procedure. Another important blood typing application involves lymphocyte cell surface antigen identification, for purposes of transplantation matching and disease-state correlation (reference 15). Heretofore, a major limitation in lymphocyte cell surface typing, by complement-mediated cell lysis, has been high non-specific cell lysis which interferes with microscopic examination of the lysed cells. The complement preparation of the invention is also applicable to the field of blood cell transplantation, in which a mixed population of cells is enriched for a desired transplant cell type by ligand-specific lysis of non-transplant cell types. The complement preparation of the invention, by reducing non-specific cell lysis, would produce greater enrichment of the transplant cells.

The complement preparation is readily and inexpensively prepared, either by adding lipid vesicles directly to complement, or by adding the vesicles and complement separately to a cell lysis system. When the serum and lipid vesicle components of the preparation are mixed together, the preparation is stable at refrigerator temperatures for up to several days, and may be stored in lyophilized form at freezer temperatures for several weeks.

IV. Homogeneous Immunoassays

According to another important aspect of the invention, there is provided an improved homogeneous immunoassay system for the determination of a ligand-related analyte. The system includes lysable lipid membrane cells (Section I), such as liposomes or biological cells, having surface-bound ligand molecules, and containing encapsulated reporter which is detectable on cell lysis. Ligand-specific cell lysis occurs in the presence of a serum source of complement (Section III) and an anti-ligand also contained in the system. Lipid vesicles (Section II) adapted to increase the ratio of ligand-specific to non-specific cell lysis are present in an amount which increases such specific to non-specific ratio more than about 2-fold over that achievable in the system in the absence of the vesicles. Preferably the vesicles are contained in an amount which increases such ratio at least about 4-fold.

In one general class of immunoassays, the analyte is the anti-ligand itself, whereby increased amounts of added analyte produce increased ligand/anti-ligand binding on the target cells and increased cell lysis. The assay reaction is carried out in a suitable reaction medium whose pH and ionic strength are compatible both with ligand/anti-ligand binding and with complement-mediated target cell lysis. Additionally, the pH and/or ionic strength may be adjusted to achieve desired surface charge characteristics in either the target cells, the lipid vesicles or both. The osmolarity of the reaction medium is adjusted in relation to the osmolarity of the interior cell spaces of the target cells, to produce a desired osmolarity gradient across the target cell membranes. This osmolarity gradient will effect the flow of solutes out of or into the target cell upon cell lysis. One preferred reaction medium, employed particularly in an assay system containing liposomal target cells, include 20 mM phosphate buffer, pH 8.0, adjusted with glucose to the same osmolarity as the interior spaces of the target cells, e.g., an osmolarity of between about 430–435 milliosmole (mosm).

The concentration of target cells in the system is preferably adjusted such that the percent of ligand-specific reporter, or marker, release from the cells continues to increase with the addition of increasing amounts of analyte within the concentration range of analyte to be tested. Similarly, the concentration of complement is preferably such that increased amounts of added analyte, within the analyte range to be tested, is reflected by increased amounts of target cell lysis and reporter release. Typical target cell concentrations for REV-type target cells are in the range between about $10^{-12}$ and $10^{-7}$ moles lipid per ml total assay volume. Complement is typically added to a final concentration of between about 2 and 100 microliters of undiluted complement serum per ml assay volume.

According to an important feature of the invention, the lipid vesicles are added in an amount which increases the ratio of ligand-specific to non-specific lysis (occurring in the absence of added anti-ligand) at least about 2-fold, and preferably at least about 4-fold, over that achievable in the system, under substantially the same conditions in the absence of added vesicles. The optimum vesicle concentration is that which maximizes the signal-to-noise ratio in the assay, i.e. the ligand-specific to non-specific lysis ratio. At a suboptimal lipid vesicle concentration, the signal-to-noise ratio will be suboptimal because of high non-specific lysis. At too high a lipid vesicle concentration, inhibition of specific lysis may occur, also tending to reduce the signal-to-noise ratio from an optimal level. The desired range of vesicle concentrations can be readily determined by titrating the assay system with increasing amounts of lipid vesicles until optimal ligand-specific to non-specific lysis ratio is achieved.

As will be recalled from Section III, and as is shown in Example VI, relatively more lipid vesicles are required to inhibit non-specific lysis in a system containing a greater concentration of complement. At typical complement concentrations noted above, maximal signal-to-noise ratios are achieved at SUV concentrations between about 0.05 and 5 micromoles lipid per ml of assay volume. Lipid vesicles comprising MLV's or REV's should be present at roughly 8 times these concentrations. In a immunoassay system containing erythrocyte target cells, where the lipid vesicles include erythrocyte ghosts, the optimal concentration of ghosts is about 4 micrograms ghost lipid per ml of assay volume (Example VII).

In a typical immunoassay, such as the one described in Example XI, ligand-coated target cells, such as ligand-carrying REV's, are preincubated either with buffer, for determination of non-specific lysis, or with the anti-ligand analyte, for determination of ligand-specific lysis. Following this preincubation, a source of complement containing added lipid vesicles (the complement preparation of Section III) is added, and the complete immunoassay reaction mixture is incubated further, typically at room temperature for about 30 minutes. The percent marker release is then determined, preferably, by calculating the ratio of measured reporter in the reaction mixture before and after the addition of a cell lytic agent, such as a detergent, which acts to release substantially all of the reporter from the target cells. The percent marker release may further be corrected for background reporter level not related to the presence of complement in the assay system, as will be described in Example III.

Several of the following examples illustrate an immunoassay system containing target-cell REV's having bound DNP ligand and encapsulated CF, guinea pig complement serum containing SUV's of various compositions, and anti-DNP antibody analyte. The degree of enhancement of signal-to-noise ratio, with respect to an immunoassay system not containing added SUV's, ranges between about 4- and 15-fold. The increased signal-to-noise ratio permits more positive identification of analyte, and detection of the analyte at a substantially lower concentration. Example XI illustrates an immunoassay whose sensitivity is roughly four times greater than that of an immunoassay which contains no SUV's. An immunoassay containing REV's having bound theophyllin-PE ligand and encapsulated CF, for the determination of anti-theophyllin anti-ligand analyte, is described in Example XIV below. The presence of SUV's of a selected lipid composition increase the signal-to-noise ratio in the assay about 10-fold over that in the absence of added SUV's.

Example VII below illustrates an immunoassay employing erythrocyte target cells for use in determination of hemolysin, an anti-ligand capable of binding specifically to erythrocyte antigens. The presence of erythrocyte ghosts in the immunoassay increased the signal-to-noise ratio about 3-fold over that seen in the absence of added lipid vesicles.

A second general class of immunoassays involves competitive inhibition between a ligand or ligand-like analyte and target cell ligands for binding to the anti-ligand in the assay. Here, the addition of increased amounts of analyte "tie up" more of the anti-ligand, with the result that less target cell lysis is produced. The various considerations relating to assay medium, concentrations of assay components, and methods for determining percent marker release discussed above are generally applicable to the inhibition test. Example XII below describes a cell lysis inhibition test in which the analyte, DNP-lysine, competes with DNP carried on REV target cells for binding to anti-DNP contained in the assay mixture. As will be seen in the example, the immunoassay system containing complement and added SUV's is about 4 times more sensitive, and also more reliable for quantitative determinations of added analyte, than the assay system which does not have added SUV's.

In a third general class of immunoassays, a bivalent analyte is adapted to bind immunospecifically with target cell binding molecules, thus attaching analyte to the cell surface. Anti-ligand in the assay then binds specifically with cell-bound analyte to activate complement-mediated lysis. An example of this class of sandwich-type assay is one adapted to detect human chorionic gonadotropin (hCG). Reaction of the analyte with target cell hCG binding proteins, e.g., anti-hCG antibody Fab fragments, produces a cell surface ligand consisting of the hCG/hCG-binding molecule complex. Addition of anti-hCG antibody to the cells then leads to complement mediated cell lysis, in proportion to the amount of hCG present.

The immunoassay of the present invention is intended for use in the determination of a variety of analytes, including serum analytes such as antigens, antibodies, or xenobiotics (e.g., drugs) contained in blood. Where the analyte is contained in serum sample, the immunoassay includes potential interference factors in both the complement serum source and the analyte-containing serum. A number of experiments conducted in support of the present invention, and described generally in Examples XIII–XVIII below, show that human serum, even in the absence of added complement, produces high levels of non-specific target-cell lysis. The examples also demonstrate that non-specific lysis can be substantially reduced by adding lipid vesicles to the serum sample, preferably before the serum sample is mixed with the target cells. In particular the experiments reported in Examples XIII and XIV show that non-specific lysis levels of about 50% can be reduced, by the addition of SUV's having a selected lipid composition, to less that about 8%, without substantially reducing levels of ligand-specific lysis. The experiments reported in Example XV illustrate the variation in non-specific cell-lysis produced by added human serum on target cell REV's having different PE derivative compositions. Also as described in Example XV, heat treating human serum to inactivate complement eliminated a substantial portion of the non-specific lysis, thereby implicating complement activating factors in non-specific target-cell lysis. However, addition of SUV's to human serum generally resulted in significantly less non-specific lysis than heat-treated serum, suggesting that human serum contains interfering factors whose lytic action is not mediated by complement, but which are effectively inhibited by the presence of the added SUV's.

That the lipid vesicles, when included in an immunoassay of the type described, are effective in inhibiting non-specific lysis due to both the serum source of complement and the added human serum, is demonstrated in Example XVI. The immunoassays in this example were performed by preincubating target-cell REV's with human serum containing added SUV's, either in the presence or absence of added anti-ligand. Levels of non-specific and ligand-specific REV lysis produced after the addition of diluted complement serum (containing no added lipid vesicles) was measured after a 30 minute incubation. As will be seen in Example XVI, added SUV's reduced the level of non-specific lysis produced by both serum sources more than 5-fold. The ability of SUV's added to the immunoassay to inhibit interference from both analyte and complement serum obviously simplifies the immunoassay procedure.

The serum and lipid-vesicle components (not including target-cells) in an immunoassay of the type just described, are also referred to herein collectively as a blood fluid composition. The composition may include the serum source of complement alone plus added lipid vesicles, i.e., the components of the above-described improved complement preparation, the analyte serum sample alone plus added lipid vesicles, or a combination of a complement source and analyte sera plus lipid vesicles added either serially or simultaneously to the two sera. Blood fluid composition also refers more generally herein to any blood fluid, such as a serum or plasma sample, which is adapted to be added to a suspension of lysable target cells to complete a cell lysis system, where the composition includes blood fluid containing at least one of the non-target cell components in the system, and lipid vesicles added to the blood fluid to increase the ratio of ligand-specific to non-specific cell lysis which occurs in the system.

The present invention provides a convenient homogeneous immunoassay, adaptable to the three assay classes described above, and for use in determining a wide range of ligand-related analytes, including those contained in a blood fluid. The several-fold inhibition of non-specific lysis achieved in the assay solves a major limitation in prior art homogeneous immunoassays of high variability related to the age and condition of the assay components, and relatively poor sensitivity due to low signal-to-noise ratio.

Like the complement preparation described above, the immunoassay components can be stored readily as individual components over periods of several months. The lipid vesicles are readily and inexpensively prepared, and can be tailored both in terms of lipid composition and surface-bound ligands for use with different types of target cells and/or analytes. The lipid vesicles appear to effectively inhibit serum interference factors whose lytic activities are not mediated by complement pathways, as well as those that are.

The invention further includes a kit for the determination of a ligand-related analyte in the immunoassay system described above. The kit includes target cells having surface bound ligand molecules, a serum source of complement capable of mediating target cell lysis in the presence of anti-ligand, and a suspension of lipid vesicles which, when mixed with the cells, complement and anti-ligand, increases the ratio of ligand-specific to non-specific cell lysis by at least 2-fold over that ratio achievable under the same conditions in the absence of the added vesicles.

Another aspect of the invention is an improved method for achieving ligand-specific lysis of lysable lipid membrane cells in the presence of complement and a soluble anti-ligand. According to the general procedures discussed above, the method includes providing a serum source of complement and lipid vesicles of the type described, and reacting the cells, and anti-ligand, and the complement with an amount of the vesicles which increases the ligand-specific to non-specific ratio at least about 2-fold over that achievable under the same conditions in the absence of the vesicles.

The following examples illustrate various aspects of the invention, but are in no way intended to limit the scope thereof.

EXAMPLE I

Preparation of Target Liposomes

Target-cell REV's encapsulating 6-carboxyfluorescein (CF) were prepared from one of the seven lipid compositions shown in TABLE I below. The lipid abbreviations in the table are: phosphatidylcholine (PC), including distearoyl (DS) phosphatidylcholine, obtained from Avanti Polar Lipids (Birmingham, AL); phosphatidylglycerol (PG); cholesterol (CHOL); alpha-tocopherol (aT), obtained from Sigma Chemical Company (St. Louis, MO); and phosphatidylethanolamine (PE) (transesterified egg PE) or PE derivatives including N-dinitrophenylaminocaproyl phosphatidylethanolamine (PE-DNP), obtained from Avanti Polar Lipids, Lot No. DCPE-23, N-[4-(P-maleimidophenyl)butyryl]phosphatidylethanolamine (PE-MPB) prepared according to the method of reference 12; phosphatidylethanolamine succinate (PE-$CO_2$H); and phosphatidylethanolamine-theophylline conjugate (PE-Th). CF, obtained from Eastman Kodak (Rochester, NY), was twice recrystallized from ethanol and further purified by molecular sieve chromatography, according to known methods.

Suspensions of REV's were prepared by the reverse phase evaporation method described generally in references 10 and 11. For each of the seven lipid compositions shown in TABLE I, micromolar amounts indicated in TABLE I for each of the lipids were dissolved in 1 ml of diethylether. To this lipid solution was added 300 microliters of an aqueous buffer solution containing 20 mM phosphate buffer, pH 8.0, 200 mM CF, having an osmolarity of about 430 mosm. The two phases were emulsified by sonication for one minute at 25° C. in a bath sonciator. Ether was removed under reduced pressure at room temperature to form an aqueous suspension of REV's encapsulating CF at an approximate concentration of 200 mM. Non-encapsulated CF was separated from the vesicles by centrifuging the vesicle suspension at 18,000 rpm for 30 minutes at 4° C. The vesicle pellet was resuspended in the above phosphate buffer (less CF), adjusted to an osmolarity of about 430 mosm with glucose, to a final lipid concentration of about 1.0 micromoles per ml. Each of the seven REV preparations were stored at 4° C. until used.

TABLE I

| Composition | REV Lipid Composition | | | | |
| --- | --- | --- | --- | --- | --- |
| | PC | PG | CHOL | aT | PE |
| 1 | 4.4 (DS) | 1 | 4 | 0.1 | — |
| 2 | 4.4 (DS) | 1 | 4 | 0.1 | 0.5 (PE—DNP) |
| 3 | 4.1 (DS) | 1 | 4 | 0.1 | 0.5 (PE—MPB) |
| 4 | 4.1 (DS) | 1 | 4 | 0.1 | 0.5 (PE—$CO_2$H) |
| 5 | 4.1 (DS) | 1 | 4 | 0.1 | 0.1 (PE—Th) |
| 6 | 4.1 (DS) | 1 | 4 | 0.1 | 1.0 (PE) |
| 7 | 4.4 | 1 | 3 | — | 0.5 (PE—DNP) |

EXAMPLE II

Preparation of MLV's and SUV's

Suspensions of multilamellar vesicles (MLV's) and small unilamellar vesicles (SUV's) having the lipid compositions designated 1-14 shown in TABLE II, and an additional lipid composition no. 15, which is similar to that of erythrocyte ghosts, were prepared. The lipid abbreviations in TABLE II, as well as the source of the lipids are the same as those in Example I. The lipids making up composition 15 include PC, bovine sphingomyeline (SM), bovine phosphatidylserine (PS), PE and PE-DNP. The micromolar amounts of these lipids were PC:3, SM:1, PS:8, PE:7, and PE-DNP:0.5.

For each of the 15 different lipid compositions, the micromolar amounts of the various lipids shown in TABLE I for samples 1-7, in TABLE II for compositions 8-14, and as given above for composition 15 were dissolved in 1 ml chloroform and dried in a glass tube under a stream of nitrogen. To each tube was added 1 ml of the suspension buffer containing 20 mM NaPO$_4$, pH 8.0, adjusted to 430 mosm with glucose. Each tube was agitated by vortexing to produce a suspension of multilamellar vesicles MLV's having a size range of between about 0.5 to 20 microns and predominantly between about 0.5 and 2.0 microns.

TABLE II

| Composition | PC | PG | CHOL | aT | PE |
|---|---|---|---|---|---|
| 1-7 | | | in TABLE I | | |
| 8 | 10 | — | — | — | — |
| 9 | 7 | — | 3 | — | — |
| 10 | 7 | 3 | — | — | — |
| 11 | 9 | 1 | — | — | — |
| 12 | 4 | 3 | 3 | — | — |
| 13 | 6.5 | 3 | — | — | 0.5 (PE—DNP) |
| 14 | 3.5 | 3 | 3 | — | 0.5 (PE—DNP) |

To prepare SUV suspensions having one of the fifteen different lipid compositions, the corresponding unfiltered suspension from above was sonciated in a bath sonicator, maintaining the suspension at about room temperature, until the suspension was optically clear, indicating that a preponderance of the vesicles having diameters less than about 0.2 microns. The sonication times typically were between 30 and 45 minutes. The SUV preparations were extruded through 0.22 micron polycarbonate filters and stored at 4° C. until used. Both the MLV and SUV preparations have a final lipid concentration of about 10 micromoles per ml.

EXAMPLE III

Effect of SUV's on Different Serum Sources of Complement

The levels of non-specific cell lysis of target-cell REV's produced by different serum sources of complement in a cell lysis system, and the reduction in non-specific lysis achievable by adding SUV's to the complement sources is discussed in the present example.

The sources of complement were guinea pig serum from Miles Lab (Elkhart, IN), Lot. No. 0051, Flow (Inglewood, CA) Lot No. GB72204B and Cappel (Cochranville, PA) Lot No. 18491. Each complement source was supplied in the form of lyophilized serum and was reconstituted to original volume with a solution provided by the supplier. Control complement samples were prepared by diluting reconstituted serum 1:10 with assay buffer containing 20 mM sodium phosphate buffer, pH 8.0 adjusted to 430 mosm with glucose. A first group of SUV-containing complement samples was prepared by diluting reconstituted serum 1:1 with a suspension of composition-7 SUV's (Example II) and diluting the SUV/complement mixture 1:5 with the above assay buffer (Example II) to a final lipid concentration of about 1 micromoles lipid/ml. This group is designated C:SUV (1:1) in TABLE III. A second group of SUV-containing complement samples, designated C:SUV (1:10) in TABLE III, was prepared by diluting reconstituted serum 1:10 with a suspension of composition-7 SUV's to a final lipid concentration of about g micromoles/ml. Target cells for the assay system were prepared by diluting a suspension of composition-7 CF-containing REV's, (Example I) 1:20 with assay buffer to a final concentration of about 0.5 micromoles lipid per ml.

In each assay, 5 microliters of diluted target-cell REV's were mixed with 25 microliters of one of the three control or treated complement samples and 25 microliters of assay buffer. Each test mixture was incubated for 30 minutes at room temperature. The reaction was terminated by the addition of 2 ml of assay buffer.

The CF fluorescence of a diluted reaction mixture ($F_{exp}$) was determined spectrophotometrically, at an excitation wavelength of 492 nm and an emission wavelength of 520 mm. 100 microliters of 10% Triton X-100 was added to the diluted reaction mixture and the total fluoresence ($F_{total}$) was similarly measured. The $F_{total}$ value was corrected by a suitable dilution factor.

In order to correct for CF background fluorescence due to REV leakage in the absence of added assay factors, 5 microliters of the diluted assay REV's were diluted to 80 microliters with assay buffer, incubated for 30 minutes, diluted with 2 ml of buffer, and read flurometrically, as above, before and after the addition of 100 microliters of Triton X-100 to give $F_{rev}$ and $F_{rev,total}$ values, respectively. If the percent marker release of REV's, in the absence of additional assay components, ($F_{rev}/F_{rev,total} \times 100$), was greater than about 10, the REV's were washed by centrifugation at 18,000 rpm for 20 minutes at 4° C. and resuspended in original volume of the assay buffer.

The percent non-specific CF release, corrected for background CF, was calculated from the following equation:

$$\% \text{ lysis} = \frac{(F_{exp}/F_{total}) - (F_{rev}/F_{rev,total})}{1 - (F_{rev}/F_{rev,total})}$$

The calculated % non-specific marker release values are shown in TABLE III.

TABLE III

| | % Non-Specific Marker Release | | |
|---|---|---|---|
| | control | C:SUV(1:1) | C:SUV(1:10) |
| Miles | 16 | 7 | 2 |
| Cappel | 30 | 3 | 1 |
| Flow | 45 | 18 | 9 |

It is seen that each of the three diluted serum sources of complement produced relatively high levels of non-specific target cell lysis, ranging from 6% to 45%, at the serum concentration used in each assay mixture. A significant decrease in non-specific marker release was achieved by the addition of the SUV's to the assay mixture, with greater inhibition of non-specific lysis being achieved at greater SUV concentrations (comparing the middle and right-hand columns). At the higher SUV conoentration (1:10), the SUV's inhibited non-specific lysis 8-fold, 30-fold and 5-fold over the corresponding untreated Mills, Cappel and Flow serum complement sources, respectively.

EXAMPLE IV

Specific and Non-Specific target Cell Lysis With SUV-Treated Complement

The present example examines non-specific and ligand-specific target cell lysis levels in an immunoassay system containing SUV complement plus added SUV's. Specific target-cell lysis was measured both in a direct ligand/anti-ligand binding assay, and in an inhibition assay in which specific cell lysis produced by binding of an anti-ligand to the target cells is inhibited by the addition to the system of soluble ligand.

The target cells employed in the assays were prepared by diluting composition-7 CF-containing REV's (Example I) 1:20 with assay buffer (described in Example III) to a final concentration of 0.5 micromoles lipid per ml. Complement samples were prepared by diluting reconstituted guinea pig serum obtained from Miles, Lot No. 0051, 1:10 with either assay buffer (control) or composition-g SUV's (Example II).

Rabbit anti-DNP-bovine serum albumin (anti-DNP-BSA) was obtained from Miles Lab (Elkhart, IN), Lot No. R658, and was reconstituted to about 1.4 to 1.8 milligrams antibody per ml. The antibody was diluted 1:100 with an antigen/antibody buffer composed of 20 mM phosphate, pH 7.4, containing 150 mM NaCl, 0.25 mM $MgCl_2$ and 0.075 mM $CaCl_2$. N-2,4-DNP-L-lysine (DNP-Lysine) used in the inhibition studies was obtained from Sigma Chemical Company (St. Louis, MO), Lot No. 22F-0397 and was dissolved to a final concentration of about $10^{-13}$ to $10^{-14}$ moles per ml in the antigen/antibody buffer.

Non-specific lysis was determined by mixing 5 microliters of CF-REV's with 25 microliters of either the 1:10 complement source or the 1:10 complement/SUV preparation and 50 microliters of assay buffer. The mixture was incubated for 30 minutes at room temperature and the reaction terminated by the addition of 2 ml of buffer. Percent marker release was determined flurometrically, as described in Example III, and corrected for background fluorescence, also as described. As seen from the data in TABLE IV below, the addition of composition 9 SUV's to the diluted complement source reduced non-specific cell lysis about 4-fold.

The direct antibody immunoassay was performed by mixing 5 microliters of diluted CF-REV's with 25 microliters of anti-DNP-BSA. After incubating this mixture for 10 minutes, 25 microliters of assay buffer, followed by 25 microliters of complement serum diluted 1:10 with either buffer or SUV's was added, and the reaction mixture incubated for an additional 30 minutes at room temperature. The reaction was terminated by the addition of 2 ml of buffer. Cell lysis, expressed as percent marker release, was calculated as above. The data, which are given in the column designated "specific", show that the presence of SUV's in the assay reaction had no inhibitory effect on specific lysis, and in fact, gave a slightly higher ligand-specific assay value. It is seen from the data that the signal-to-noise ratio, calculated as the ratio of specific to non-specific percent marker release, increased from less than about 3 for the assay containing untreated complement to a value of greater than 12 in the assay containing added SUV's.

TABLE IV

| | % Marker Release | | |
| --- | --- | --- | --- |
| | non-specific | specific | sp. inhib. |
| control | 27 | 73 | 70 |
| SUV (#9) | 7 | 87 | 92 |

The antigen-inhibition assay tests were performed by incubating 5 microliters of the diluted REV's with 25 microliters of anti-DNP-BSA, and 25 microliters of DNP-lysine, for 10 minutes at room temperature. Following this, 25 microliters of complement source diluted 1:10 either with buffer or SUV's was added and the reaction mixture incubated for an additional 30 minutes at room temperature. As above, the reaction was terminated by the addition of 2 ml of buffer and % marker release before and after the addition of 100 microliters of Triton X-100, corrected for background fluorescence, was calculated. The specific inhibition values, which are shown in the right-hand column in TABLE IV, represent the percent reduction in specific lysis observed when DNP-lysine is added to the system containing DNP-coated REV's, anti-DNP and complement. As seen from the data, the addition of SUV's to the complement source had no inhibitory effect on the degree of ligand inhibition observed, and in fact, even increased ligand-specific inhibition slightly.

EXAMPLE V

Effect of SUV Lipid Composition On Complement Treatment

The specific and non-specific lytic activity of complement containing SUV's of different lipid compositions was measured. SUV's having composition 7–12 shown in TABLE II, were prepared in accordance with Example II. Miles guinea pig serum, Lot No. 0051 was diluted 1:10 with either assay buffer (control) or one of the seven SUV lipid compositions noted in TABLE V.

The extent of non-specific lysis was determined, for the control and for each of the different SUV lipid compositions, in an assay test substantially identical to that described in Example III. Five microliters of diluted composition-7, CF-containing REV's prepared in accordance with Example I, were mixed with 25 microliters of the diluted complement source, and 50 microliters of assay buffer, and the assay solution was incubated for 30 minutes at room temperature. Percent marker release was determined as in Example III. As seen from the middle column in TABLE V, the different-lipid composition SUV's, when added to complement in the assay system, reduced the extent of non-specific lysis from a control value of 27% to levels ranging between 1% and 7%.

The extent of specific lysis in a assay system containing CF-REV's and anti-DNP-BSA was determined substantially in accordance with the method detailed in Example IV. Five microliters of diluted REV's were mixed with 25 microliters of the anti-DNP-BSA solution from Example IV, preincubated for 10 minutes, after which 25 microliters of complement diluted with buffer or one of the six SUV compositions and 25 microliters of assay buffer were added, and the assay reaction mixture incubated for 30 minutes. Percent marker release values calculated as above, are shown in the right-hand column in TABLE V.

TABLE V

| Composition | % Marker Release non-specific | specific |
|---|---|---|
| — | 27 | 73 |
| 7 | 6 | 85 |
| 8 | 7 | 85 |
| 9 | 7 | 87 |
| 10 | 3 | 2 |
| 11 | 3 | 40 |
| 12 | <1 | 24 |

Compositions 7, 8 and 9, all of which produced substantial reductions in non-specific activity, all showed high ligand-specific activity. The data indicate that in an assay system containing REV's having PC as a major lipid component, SUV's composed exclusively of PC (composition 8), or PC:cholesterol in a 7:3 molar ratio (composition 9) appear to be as effective as composition-7 SUV's which include, in addition to PC, and cholesterol, PG and PE-DNP components also present in the target composition-7 REV's.

By contrast, SUV's of composition 10-12, containing either 10 or 30 mole percent negatively charged PG, all produced significant inhibition of the percent of specific marker release, with composition-10 SUV's, composed of PC and PG in a 7:3 molar ratio, producing substantially complete inhibition of specific marker release. The inhibition apparently due to PG in composition 10-12 SUV's was not observed in composition-7 SUV's which also contain PG.

EXAMPLE VI

Effect of Relative SUV and Complement Source Concentrations

Composition-7 SUV's were prepared as described in Example II. Reconstituted complement serum, obtained from Miles, Lot No. 0051, was diluted 1:10, 1:100 or 1:500 with assay buffer (control) or assay buffer plus aliquots of the SUV suspension to produce the SUV assay concentrations indicated at the left-hand column in TABLE VI.

Non-specific lysis assays were performed by preincubating 5 microliters of diluted composition-7 CF-containing REV's with 50 microliters of buffer for 5 minutes, followed by the addition of 25 microliters of one of the fifteen different complement or SUV-containing complement samples indicated in TABLE VI. Each reaction mixture was incubated for 30 minutes and the percent non-specific marker release was determined as in Example III. The percent marker release values are shown in TABLE VI.

TABLE VI

| SUV's umole lipid/ml | % Non-Specific Release Complement-dilution | | |
|---|---|---|---|
| | 1:10 | 1:100 | 1:500 |
| control (−SUV) | 44 | 34 | 7 |
| .02 | 40 | 28 | 3 |
| .04 | 41 | 25 | >1 |
| .2 | 35 | 4 | >1 |
| 2.0 | 12 | 2 | >1 |

As seen, there is a substantial and systematic reduction in the extent of non specific lysis when either the concentration of complement is reduced, or the concentration of SUV's added to the complement is increased. The data indicate that the relative SUV and complement concentrations in a cell lysis system can be adjusted to produce an desired reduction in non-specific lysis.

EXAMPLE VII

Lipid Vesicle/Target Cell Compatibility

The requirement for target cell/lipid vesicle compatibility in liposomes having substantially different lipid compositions, and in biological cells, was examined. The following target cells were prepared: composition-7 REV's, artificial ghost (AG) REV's, and sheep red blood cell erythrocytes. Composition-7 REV's and artificial ghosts REV's each containing encapsulated CF, were prepared substantially as described in Example I. The lipid composition of AG-REV's was substantially like that of sheep red blood cell membranes, and included PC, sphingomylin (SM), phosphatidyl serine (PS), and PE-DNP in a ratio of 3:1:8:7:0.5. Sheep red blood cells, obtained in Alsever's solution from Microbiological Media (San Ramon, CA), were prepared as described below.

Corresponding-composition lipid vesicles were: Composition-7 SUV's, SUV's having the above-described composition of artificial ghosts (AG-SUV's), and sheep red blood cell ghosts. The two SUV's preparations were prepared substantially as described in Example II. Sheep red blood cell ghosts were prepared by washing the above red cells several times in isotonic buffer, osmotically lysing the cells in hypotonic buffer at 4° C., and reannealing the lysed cells by incubation at 37° C., according to a standard procedure. Reconstituted guinea pig serum from Miles Lab, Lot #0051, was diluted 1:10 with assay buffer (control), with composition-7 or AG SUV's to concentrations of about 1 micromole lipid per ml complement sample, or with erythrocyte ghosts to a final membrane lipid concentration of about 4 micromoles lipid per ml complement sample.

Non-specific and specific marker release in composition-7 and AG REV's in the presence of control or one of the two SUV-containing complement samples were determined as follows: 5 microliters of one of the diluted CF-containing REV's were mixed with 25 microliters of buffer (non-specific lysis) or 25 microliters of anti-DNP antibody (specific lysis) from Example III. The mixtures were incubated for 10 minutes, after which was added 25 microliters of buffer followed by 25 microliters of one of the four complement samples indicated in the left-hand column in TABLE VII. After incubating the various assay mixtures for 30 minutes, the extent of non-specific marker release, corrected for CF background, was determined as in Example III. The data obtained, expressed as a ratio of non-specific to specific marker release, is shown in the second and third columns in TABLE VII.

Looking first at the data relating to the composition-7 REV's, it is seen that composition-7 SUV's produce about a 5-fold reduction in non-specific lysis without appreciably effecting specific lysis, similar to what has been reported above. Interestingly, AG-SUV's, which have a relatively high negative surface charge, also significantly reduce non-specific lysis without affecting specific lysis. By contrast, red blood cell ghosts gave a slightly higher level of non-specific activity than untreated (control) complement, while producing no significant effect on specific lysis.

TABLE VII

| vesicles | target cells, with % marker release | | (unsensitized/ sensitized) |
|---|---|---|---|
| | (non-specific/ specific) | | |
| | 7-REV | AG-REV's | SRBC |
| Control | 20/84 | 27/14 | 26/80 |
| Composition-7 | 4/85 | 19/2 | 31/81 |
| A.G. | 7/83 | 4/0 | 29/87 |
| Ghosts | 27/83 | 37/14 | 6/56 |

The data in the third column in TABLE VII, relating to specific and non-specific marker release from AG-REV's, show a very low level of specific cell lysis for all four different complement samples examined. Each of the two types of SUV's used to treat complement reduced non-specific lysis, but at the same time almost completely eliminated specific lysis. Red blood cell ghosts had the effect of increasing non-specific lysis, without appreciably effecting the level of specific lysis, similar to its effect on non-specific and specific lysis of composition-7 REV's. The data in column 3 underscore the fact that where the target cells—in this case, AG-REV's—themselves do not yield high specific lysis values, treating complement with vesicles such as SUV's to produce non-specific lysis may not enhance the signal-to-noise ratio in the assay.

The assays involving sheep red blood cells as target cells were carried out to determine the extent of lysis, in the presence of the various complement samples above, of unsensitized sheep red blood cells and cells sensitized with hemolysin, a cell-specific antibody. Hemolysin, lot #74122 was obtained from Cordis Labs (Miami, FL).

To prepare unsensitized cells, sheep red blood cells in Alsever's Solution were washed two times in buffer A containing 20 mM phosphate, pH 7.4, 150 mM NaCl, pelleting the washed cells by centrifugation at 2,500 rpm. The pelleted cells were then washed once with buffer B containing, in addition to the buffer A components, 0.25 mM $MgCl_2$ and 0.075 mM $CaCl_2$. After centrifugation and removal of the supernatant, enough buffer B was added to make a 2.8% cell suspension.

Sensitized cells were prepared by washing sheep red blood cells three times in buffer A, and preparing a 2.8% suspension of the cells in buffer A. An equal volume of hemolysin diluted 1:10,000 was added dropwise to the cell suspension, and incubated for 15 minutes at 37° C. in a water bath with shaking. The hemolysin-treated cells were washed two times in buffer A followed by a final wash in buffer B, and resuspended in buffer B to 2.8% cell suspension.

The sheep red blood cell lysis assays were performed by mixing 0.1 ml complement diluted 1:10 with 0.1 ml of buffer B (control) or one of the three vesicle fractions, to a final vesicle concentration of 1 micromoles lipid per ml of composition-7 or AG vesicles, or 4 micromoles lipid per ml of erythrocyte ghosts. An assay blank included 0.2 ml of buffer B. The assay components were incubated for 5 minutes at room temperature. Following this, 50 microliters of a 2.8% suspension of sensitized or unsensitized sheep red blood cells were added to all of the assay tubes which were vortexed and incubated for one hour at 37° C. in a water bath with shaking. The assay reaction was terminated by the addition of 0.4 ml buffer B to all tubes, followed by vortexing and centrifugation for 10 minutes at 2,500 rpm to pellet the red blood cells.

To determine the extend of red blood cell lysis, the optical density of the supernatants from the above centrifugation step were measured at 540 nm. To determine total releasable marker, 0.025 ml of 10% solution of Nonidet-P40, a non-ionic detergent, obtained from Particle Data (Elmhurst, IL) was added to each tube, and following vortexing to lyse the red blood cells, the optical density of the samples was again read at 540 nm. This procedure was carried out for each of the test solutions, to yield an uncorrected ratio of OD before and after the addition of detergent, and for the assay blank, to yield a ratio of background cell hemoglobin release. The percent lysis, corrected for background, was calculated by a formula analogous to the one used in Example III.

The ratios of unsensitized to sensitized cell lysis are shown in the right-hand column in TABLE VII. As seen, neither of the two SUV's reduced the extent of lysis in unsensitized cells, nor appreciably enhanced the ratio of sensitized to unsensitized cell lysis. By contrast, the addition of red blood cell ghosts to the complement produced more than a 4-fold decrease in unsensitized cell lysis, while producing only about a 30% reduction in sensitized cell lysis. The signal-to-noise ratio was thus improved about 3-fold over the ratios obtained in the other three assays.

EXAMPLE VIII

Non-Specific Lysis By Complement After Removal of Added Lipid Vesicles

Lipid vesicles (MLV's) were added to a serum source of complement and were removed by centrifugation, prior to adding the complement source to a cell lysis system. A suspension of composition-7 MLV's was prepared substantially in accordance with Example II. Tritiated dipalmitoyl PC, obtained from Amersham (Arlington Heights, IL) Lot No. 9-25 MBq, was included in the MLV's to a final radioactivity of 10,000 cpm per micromole lipid. Serum complement obtained from Miles Lab, Lot No. 0051, was diluted 1:10 with assay buffer (control) or with the MLV suspension to a final lipid concentration of 4 micromoles lipid per ml. Ficoll, obtained from Sigma (St. Louis, MO) was added to both complement samples to a final concentration of 20% Ficoll. Both Ficoll-containing complement samples were tested for specific and non-specific REV lysis, according to the assay procedure described in Example III. The measured marker release values are shown in the first two rows in TABLE VIII. As seen, the addition of MLV's to complement reduced non-specific marker release nearly 2-fold without appreciably affecting specific lysis marker release.

MLV's were removed from the MLV-containing serum source by high speed centrifugation for one hour. In the experiment, both control and MLV-containing complement samples in 20% Ficoll were overlayed in an ultracentrifugation tube with a 10% Ficoll layer and an upper assay buffer. The gradient samples were centrifuged at 100,000 x g for one hour, and the following discontinuous gradient fractions were removed carefully by aspiration: fraction #1, containing the upper assay buffer; fraction #2, a lipid-containing interface between the assay buffer and the 10% Ficoll layer; fraction #3, containing the 10% Ficoll layer; and fraction #4, containing the serum source in 20% Ficoll. Approximately 86% of the MLV's added to the complement was recovered in interface fraction #2 as evidenced by lipid vesicle radioactivity level. Almost all of the complement activity remained in the lower 20% Ficoll fraction (#4).

The two #4 fractions, containing either control or MLV-treated complement source in 20% Ficoll, were each tested for levels of specific and non-specific REV lysis in a test system like that detailed in Example III.

TABLE VIII

|  | % marker release (non-specific/specific) |
|---|---|
| control (−MLV) | 60/70 |
| control (+MLV) | 36/72 |
| fraction 4 (−MLV) | 67/73 (+MLV) 40/69 |
| fraction 4 (+MLV) | 56/79 (+MLV) 36/53 |

As seen in TABLE VIII, fraction #4 control complement (third row) produced about the same levels of non-specific and specific lysis as did the control complement prior to centrifugation (first row). When MLV's were added to the control fraction #4 complement, the levels of non-specific and specific REV lysis shown at the right in Row 3 were obtained. These values are roughly comparable to the values obtained for the uncentrifuged complement containing MLV's (Row 2), indicating that the centrifugation step itself did not significantly affect the lytic activity of the complement source or its activity in the presence of added MLV's.

The ratio of non-specific to specific lysis produced by complement to which MLV's had been added and subsequently substantially removed by centrifugation is shown in the center column of the fourth row. The level of non-specific lysis observed was only slightly less than that observed for complement which had not been treated with MLV's (Rows 1 and 3), indicating that the continued presence of the added liposomes may be necessary for optimal reduction in non-specific complement-mediated lysis. Addition of fresh MLV's to the earlier-treated complement produced a significant decrease in both non-specific and specific lysis levels. The result suggests that the second MLV treatment may have partially depleted the serum of soluble components which contribute both to non-specific and specific lysis.

EXAMPLE IX

Stability of Lyophilized SUV-Containing Complement

The experiment reported herein examines the stability of a lyophilized, SUV-containing complement preparation. The complement source was obtained from Miles Lab, lot. #0051. SUV's having lipid composition-7 (Example II) plus 1% alpha-tocopherol were prepared in accordance with Example II, to a final lipid composition of 10 micromoles lipid per ml. Samples of complement diluted 1:1 with SUV buffer or with the composition-7 SUV's were lyophilized rapidly, purged with nitrogen and sealed in order to exclude moisture.

TABLE IX

| day | % marker release (non-specific/specific) | | |
|---|---|---|---|
|  | 24° C. | 4° C. | −60° C. |
| 0 control: C− SUV | 46/81 | — | — |
| 0 fresh C + SUV | 3/85 | — | — |
| 3 | 3/80 | 7/84 | 10/84 |
| 6 | 4/22 | 10/83 | 13/82 |
| 13 | 4/0 | 14/80 | 17/83 |
| 28 | — | 6/54 | 6/85 |

Sealed vials were stored at room temperature (24° C.), refrigerator temperature (4° C.) and freezer temperature (−70° C.), for periods up to 28 days. At the time intervals indicated in the left-hand column in TABLE IX above, the lyophilized, SUV-containing complement samples were reconstituted with an original volume of distilled water and tested immediately in the REV lysis system described in Example III, for levels of non-specific and specific marker release. The two complement control samples tested at day 0 (no storage) were: (1) freshly reconstituted complement diluted one to one with buffer (C-SUV) and (2) freshly reconstituted complement diluted one to one with SUV's (C+SUV). The data from these two rows are consistent with the general findings in several of the above examples.

After three days storage, all three samples showed substantially full lytic activity, although non-specific lysis was somewhat greater with the samples stored at lower temperatures. After 6 days, the lyophilized sample stored at room temperature showed a sharp decline in the ability to mediate ligand-specific REV lysis, in contrast to the samples stored at refrigerator or freezer temperatures which retained full lytic activity. By 28 days, the sample stored at refrigerator temperature began to lose significant specific lysis activity, but the sample stored at freezer temperature was substantially indistinguishable in activity from fresh SUV-containing complement.

EXAMPLE X

Stability of Reconstituted SUV-Conatining Complement

The present example examines the stability of complement samples prepared by adding SUV's to freshly reconstituted complement serum. Guinea pig serum obtained from Miles, Lot No. 0051, was reconstituted with the supplied complement diluent. An equal volume of composition-7 SUV's were added to the reconstituted complement to a final SUV concentration of about 1 micromoles lipid per ml. This complement preparation is referred to in the experiment as a concentrated solution, the relevant data being shown in the middle column in TABLE X. A portion of the concentrated solution was further diluted 1 to 10 with SUV buffer to give a dilute complement solution, the relevant data of which is shown at the right in TABLE X.

Both the concentrated and dilute SUV-treated samples were stored at 4° C., and at 1, 3 and 7 day storage periods, were tested for specific and non-specific lysis in the REV lysis test described in Example III. The results, given in TABLE X, show that both the concentrated and dilute SUV complement samples are substantially unchanged over a 3-day storage period. The two complement solutions show only a moderate increase in non-specific lysis activity after a 7-day storage period. The dilute solution shows shows a moderate decline in specific lysis activity after 7 days.

TABLE X

|  | % marker release (specific/non-specific) | |
|---|---|---|
| days | conc. | dilute |
| 1 | 3/86 | 8/85 |
| 3 | 3/88 | 3/85 |
| 7 | 12/82 | 14/61 |

The above SUV-treated complement samples were stored in glass vials. The stability of the two SUV-treated preparations, when stored in polypropylene vials, at 4° C. was also examined. Essentially the same results were obtained, except that there was no appreciable decline in specific lytic activity in the dilute solution after the 7-day storage period. Thus it may be advantageous to store a SUV-containing complement preparation in a polypropylene or other suitable plastic storage container.

In a similar type of experiment, lyophilized complement was reconstituted with complement diluent, diluted with SUV's to form either the concentrated or dilute solution described above and then lyophilized, under rapid lyophilization conditions. The lyophilized SUV-treated complement preparation was stored overnight, reconstituted with an original volume of distilled water, and then stored for periods of up to 7 days, as reported above. The amount of specific and non-specific lysis observed after 1, 3 and 7 days of storage at 4° C. was substantially identical to the reported specific and non-specific values reported in TABLE XI. Thus, lyophilizing SUV-treated complement for a period of about 12 hours appears to have little or no effect on the storageability of the complement preparation at 4° C.

EXAMPLE XI

Sensitivity of Direct Immunoassay Employing SUV-Treated Complement

The direct cell-lysis assay test described in Example IV, in which DNP specific REV lysis was produced by the addition of anti-DNP antibody to the assay mixture, was carried out in the presence of saturating or near-saturating levels of anti-DNP antibody. The present example examines the sensitivity of the direct assay test in terms of the minimum amount of added anti-DNP antibody which can be detected.

Reconstituted complement, obtained from Miles, lot #0051, was diluted 1:10 with either buffer or composition-7 SUV's to a final SUV concentration of 1 micromoles of lipid per ml complement.

The assays were performed by adding to 5 microliters of composition-7, CF-containing REV's, diluted 1:20, to 25 microliters of anti-DPN antibody, diluted to give the molar amounts shown at the left in TABLE XI. The REV/antibody mixtures were preincubated for 10 minutes at 37° C. To each mixture was added 25 microliters of diluted complement or complement plus SUV's, as indicated in the middle or right columns, respectively, in TABLE XI. The assay mixtures were incubated at room temperature for 30 minutes and the percent of non-specific and specific lysis determined as in Example III. The values obtained for specific and non-specific marker release at the various antibody concentrations indicated, are shown in TABLE XI. The low non-specific lysis value for complement alone is due, at least in part, to the conditions of the reaction components, which were selected to minimize non-specific cell lysis. Specificially the REV's were freshly prepared, and the complement had been stored for several days at 4° C.

TABLE XI

| Antibody | % Marker release | |
|---|---|---|
| (moles/assay × $10^{14}$) | Complement | Complement + SUV's |
| 0 (non-specific) | 4 | 1 |
| 2.2 | 2 | 2 |
| 22.2 | 7 | 15 |
| 29.0 | 11 | 12 |
| 44.0 | 18 | 21 |
| 88.0 | 43 | 33 |

TABLE XI-continued

| Antibody | % Marker release | |
|---|---|---|
| (moles/assay × $10^{14}$) | Complement | Complement + SUV's |
| 130.0 | 78 | 88 |
| 220.00 | 94 | 93 |

For the assay groups containing both complement alone and complement plus SUV's, a direct relation between antibody concentration and percent marker release was observed, and the actual percent marker release values were comparable in the two systems at increasing antibody levels tested. However, because the level of non-specific lysis in the system containing complement plus SUV's was about 4-fold lower than that of the system containing complement alone, the sensitivity of the assay containing added SUV's, as defined by the amount of antibody analyte which produces a dectable signal-to-noise ratio, is about 4-fold greater in the SUV-containing assay.

EXAMPLE XII

Inhibition Assay Sensitivity With Complement and SUV-Containing Complement

The present example examines the sensitivity, in terms of the minimum level of added DNP which can be detected, in an inhibition assay system of the type described in Example IV. Treated and untreated complement samples, identical to those described in Example XI, were employed. The assays were performed substantially as described in Example IV. Five microliters of diluted composition-7, CF-containing REV's were mixed with $2 \times 10^{-6}$ micromoles anti-DNP-BSA (Example IV) in 25 microliters of assay buffer, and 25 microliters of DNP-lysine (Example IV) diluted with assay buffer to produce one of the assay concentrations indicated at the left in TABLE XII. The assay mixtures were incubated for 10 minutes at room temperature, after which 25 microliters of one of the two complement samples was added. The assay reaction mixtures were incubated at room temperature for 30 minutes, and the percent specific inhibition values, calculated from the percent marker release, were determined as in Example III. The values of percent inhibition are shown in column 2 (complement alone) and in column 3 (SUV-containing complement) in the table.

It is seen from the data that in the assay system employing SUV-containing complement, as little as $2.7 \times 10^{-7}$ micromoles of DNP-lysine could be detected, and the percent inhibition is related in a substantially linear fashion with the amount of DNP-lysine added. In the assay system containing complement alone, the minimum detectable level of DNP-lysine was $11 \times 10^{-7}$ micromoles, and the assay system showed more deviation from linearity at increasing DNP-lysine concentrations. The system containing complement and SUV's is therefore about 4-fold more sensitive, and also more accurate for quantitative determinations of added inhibitor, than the system containing complement alone.

TABLE XII

| DNP-lysine | % Inhibition | |
|---|---|---|
| (umoles × $10^{-7}$/assay) | Complement | Complement + SUV |
| 2.7 | 0 | 3 |
| 5.5 | 0 | 6 |
| 11.0 | 4 | 13 |
| 22.0 | 13 | 25 |

TABLE XII-continued

| DNP-lysine | % Inhibition | |
|---|---|---|
| (umoles × $10^{-7}$/assay) | Complement | Complement + SUV |
| 44.0 | 62 | 76 |

EXAMPLE XIII

Effect of SUV's on Serum-Induced REV Lysis

Examples III–XII above involved assay systems containing CF-REV's and a serum source of complement, either in the presence or absence of specific antibodies against target cell antigens. These examples were addressed specifically to an aspect of the invention which provides an improved complement preparation, and a cell lysis systems in which the principal source of non specific cell lysis is the serum source of complement. Another potential source of interfering factors which can lead to non-specific lysis is a blood-fluid sample, such as human serum or plasma, containing analyte to be assayed in the system. The present example, and the following Examples XIV–XVIII examine the problem of non-specific REV lysis by human serum, and the reduction in non-specific lysis which can be achieved by reacting the serum and REV components in the presence of different-composition of SUV's.

Composition-2 REV's, CF-containing were prepared in accordance with Example I to a final concentration of 40 nanomoles lipid per ml. Human serum, obtained from healthy donors, was stored for 2 days at 4° C., then diluted 1:10 with assay buffer before use. Goat anti-DNP-BSA serum was obtained from Miles Labs. (Elkhart, IN) and diluted 1:10 with assay buffer. Diluted guinea pig complement, obtained from Miles Lab, lot #0051, was prepared by diluting the serum 1:10 with composition-2 SUV's (Example II) to a final lipid concentration of 1.0 micromole per ml. SUV's, compositions 1, 2 and 3 (TABLE II) were prepared in accordance with Example II to a final lipid concentration of 10 micromoles lipid per ml. The assays were performed by first mixing 25 microliters of sample—either human serum or goat anti-DNP antibody—with 5 microliters of buffer or one of the three SUV samples (50 nanomoles lipid), for 10 minutes at room temperature. Following this step, 50 microliters of composition-2 REV's (2 nanomoles lipid) were added to each reaction mixture and incubated for another 10 minutes. The lysis was induced by the addition to each assay mixture of 25 microliters of the diluted, SUV-containing complement. Thus each assay mixture contain 25 nanomoles of composition-2 SUV's and either buffer or 50 nanomoles of one of the three different composition SUV's. The total assay mixture was incubated for 30 minutes at room temperature, and the corrected percent marker release values, calculated as above (data shown in TABLE XIII).

TABLE XIII

| | % Marker Release | |
|---|---|---|
| SUV's | human serum | anti-DNP |
| control | 53 | 95 |
| composition-1 | 47.7 | 95.5 |
| composition-2 | 10 | 0 |
| composition-3 | 7.9 | 96 |

The data in TABLE XIII indicate that untreated human serum and human serum containing composition-1 SUV's produced levels of non-specific lysis which were roughly half that of ligand-specific lysis levels produced in the presence of anti-DNP-antibody. As will be recalled from TABLE I, composition-1 SUV's contain PC, PG, and cholesterol but no PE or PE derivatives. Composition-2 SUV's, which contain, in addition to the composition-1 lipids, approximately 5 mole percent of PE-DNP, strongly inhibited both non-specific lysis produced by human serum and ligand-specific lysis. As noted above, all of the assay mixtures in the experiment reported here contained 25 nanomoles of composition-2 SUV's which were added to the complement in the assays. This level of composition-2 SUV's did not appreciably affect non-specific or specific lysis (composition-1 and composition-3 data), whereas at 75 nanomoles of composition-2 SUV's, ligand specific lysis was almost completely inhibited. Data presented in Example XIV also indicate that the high concentration of SUV PE-DNP ligand in the system was responsible for the inhibition of ligand-specific lysis in the composition-2 assay. The data relating to composition-3 SUV's show that certain lipid compositions, in this case one containing PC, PG, cholesterol and PE-MPB, are capable of reducing serum-related lysis several-fold without appreciably affecting ligand-specific lysis.

EXAMPLE XIV

Lysis of Composition-5 REV's by Human Serum and Anti-Theophylline Antibody

The present example examines the relationship between REV and SUV ligand composition in an assay system in which the target-cell REV ligand is theophylline, and one of the SUV compositions present in added human serum contains surface-bound theophylline. Composition-5 REV's containing 200 mM CF, were prepared in accordance with Example I to a final lipid concentration of 40 nanomoles per ml. Anti-theophylline-BSA rabbit serum was obtained from Western Chemical Research (Fort Collins, CO). Human serum, obtained from healthy donors, was stored at 4° C. for 2 days, then diluted 1:10 wih assay buffer before use, as in Example XIII. Goat anti-theophylline serum, obtained from Western Chemical Research was diluted 1:10 with assay buffer and stored at 4° C. for 1 day. Guinea pig serum, obtained from Miles Lab, lot #0051, was diluted 1:10 with assay buffer.

Assays were carried out by mixing 25 microliters of diluted human serum or goat anti-serum sample with 5 microliters of assay buffer or with 5 microliters of one of the three different-composition SUV's shown in TABLE XIV to a lipid concentration of about 1 micromoles/ml. The mixtures were incubated for 10 minutes at room temperature, followed by the addition of 50 microliters of composition-5 REV's (2 nanomoles) and further incubation at room temperature for 10 minutes. Lysis was induced by the addition of 25 microliters of diluted guinea pig complement containing 25 nanomoles of composition-2 SUV's (Example XIII) for 30 minutes. Percent marker release values are shown in TABLE XIV.

TABLE XIV

| | % Marker Release | |
|---|---|---|
| SUV's | human serum | anti-theophylline |
| control | 43 | 83% |
| composition-1 | 31.2 | — |
| composition-2 | 22% | 82% |

TABLE XIV-continued

| SUV's | % Marker Release | |
|---|---|---|
| | human serum | anti-theophylline |
| composition-3 | 2.7% | 57% |

The data relating to control and composition-1 SUV's is consistent with that shown in TABLE XIII indicating that composition-1 SUV's are relatively ineffective in reducing serum-related non-specific lysis. Composition-2 SUV's, which contain PE-DNP, were less effective in reducing non-specific lysis in composition-5 REV's than in the composition-2 REV's used in Example XIII, but produced little or no inhibition of specific lysis, unlike that observed in Example XIII. These results support the view that composition-2 SUV's inhibited specific lysis of composition-2 REV's in Example XIII by competing with REV's for binding to anti-DNP.

Composition-3 SUV's effected an approximately 15-fold reduction in serum-related non-specific lysis, while reducing specific lysis in the presence of anti-theophylline antibody by about 30% only. The roughly 10-fold increase in signal-to-noise ratio achieved by the addition of composition-3 SUV's to the assay system described herein compares with the 6-fold increase achieved with composition-3 SUV's in the system described in Example XIII.

EXAMPLE XV

Effect of SUV's on Non-Soecific Cell Lysis Due to Fresh and Heat-Treated Serum

The degree of non-specific target cell lysis, when mixed with fresh or heat-treated human serum, either in the presence or absence of added SUV's was studied. Five REV preparations, each prepared to contain 200 mM encapsulated CF and one of the lipid compositions indicated at the left in TABLE XV below were prepared in accordance with Example II. Fresh human serum was obtained from healthy donors, and a portion of the serum was heated at 56° C. for 30 minutes to inactivate serum complement. Composition-3 and composition-6 SUV's were prepared in accordance with Example II. 25 microliters of fresh or heat-treated serum, diluted 1:10 with assay buffer, were mixed with 10 microliters of buffer or 10 microliters (100 nanomoles) of either composition-3 or composition-6 SUV's. After incubating the mixtures for 10 minutes at room temperature, 50 microliters of one of the five different-composition REV's shown at the left in TABLE XV were added to each mixture, which was then incubated an additional 30 minutes at room temperature. Note that a separate source of complement serum, such as guinea pig serum, was not included in the reaction mixtures. The reactions were terminated by the addition of 1 ml of assay buffer and the percent lysis, corrected for background fluorescence, was determined as in Example III. The results are shown in TABLE XV below.

TABLE XV

| REV's (composition) | Serum Sample | SUV's (composition) | % lysis |
|---|---|---|---|
| 1 (No PE) | fresh | — | 25 |
| | | 6 | 1 |
| | | 3 | 0 |
| | heated | — | 1 |
| | | 6 | 0 |
| | | 3 | 0 |
| 2 (PE—DNP) | fresh | — | 81 |
| | | 6 | 76 |
| | | 3 | 12 |
| | heated | — | 41 |
| | | 6 | 18 |
| | | 3 | 10 |
| 3 (PE—MPE) | fresh | — | 40 |
| | | 6 | 28 |
| | | 3 | 2 |
| | heated | — | 13 |
| | | 6 | 3 |
| | | 3 | 2 |
| 4 (PE—CO$_2$H) | fresh | — | 85 |
| | | 6 | 85 |
| | | 3 | 14 |
| | heated | — | 15 |
| | | 6 | 4 |
| | | 3 | 4 |
| 6 (PE) | fresh | — | 50 |
| | | 6 | 13 |
| | | 3 | 3 |
| | heated | — | 6 |
| | | 6 | 3 |
| | | 3 | 3 |

From the date related to composition-1 REV's, (containing no PE) it is seen that treating serum with either composition-3 or composition-6 SUV's and/or heat-treating the serum effectively elminates serum-related non-specific REV lysis. The data relating to composition-2 REV's (containing PE-DNP) shows high target-cell susceptibility to non-specific serum lysis, even after the serum has been heat treated. Maximal reduction in non-specific lysis is achieved by adding composition-3 SUV's (containing PE-MPE) to either fresh or heat-treated serum. These data suggest first, that the added serum contains appreciable amounts of non-complement (heat-stable) factors which are capable of lysing certain types of target cells non-specifically at high levels. Secondly, SUV's of composition-3 effectively inhibit both heat labile and heat stable interference factors in the serum.

The data relating to composition-3 REV's support the general conclusions above that (1) heat treating serum destroys some but not all serum factors capable of lysing REV's and (2) composition-3 SUV's effectively eliminate both heat stable and heat-labile interference factors in serum. These general conclusions also apply to the composition-6 REV's containing PE, as seen at the bottom of TABLE XV.

The composition-4 REV's show a strong susceptibility to heat-labile interference factors in serum, as can be appreciated from the data. In this example, it was found that the combination of added SUV's plus heat treatment produced a greater inhibition of non-specific lysis than either heat treatment or addition of SUV's alone.

EXAMPLE XVI

Efect of SUV-Treated Serum on Added Complement

Example XV above demonstrates that SUV's, particularly composition-3 SUV's, are effective in reducing non-specific target cell lysis caused by human serum. The present example examines whether SUV's added to human serum are also effective in reducing non-specific target cell lysis caused by added complement serum source, where the complement serum does not itself contain separately added SUV's, as was the case in example XIII and XIV.

Composition-2, CF-containing REV's, were prepared in accordance with Example I. Composition-2 and composition-3 SUV's (Example II) were prepared in accordance with Example II. Human serum, obtained from healthy donors, was stored at 4° C. for 1 week, then diluted 1:10 with assay buffer. Goat anti-DNP-BSA serum, obtained from Miles Laboratories, was diluted 1:10 with assay buffer.

Each assay was carried out by mixing 25 microliters of sample—either buffer, diluted serum or diluted anti-DNP—with 15 microliters of either buffer or composition-3 SUV's (150 nanomoles lipid). After a 10 minute incubation at room temperature, 50 microliters of composition-2 REV's (approximately 2 nanomoles REV lipid) were added to each sample which was then incubated for 10 minutes at room temperature. Following this, 25 microliters of 1:10 diluted complement, complement diluted 1:10 with composition-2 SUV's or buffer was added, and the complete assay mixture was incubated for 30 minutes at room temperature. After addition of 1 ml of buffer, the percent marker release was determined in accordance with Example III. The data are shown in TABLE XVI below.

TABLE XVI

| Sample | SUV (composition) | Complement | % marker release non-specific lysis | specific lysis |
|---|---|---|---|---|
| buffer | — | C | 21 | |
| buffer | — | C + SUV(2) | 17 | |
| buffer | +(3) | C | 3 | |
| serum | — | — | 75 | |
| serum | — | C | 76 | |
| serum | +(3) | — | 11 | |
| serum | +(3) | C | 15 | |
| serum | +(3) | C + SUV(2) | 11 | |
| anti-DNP | — | C + SUV(2) | | 79 |
| anti-DNP | +(3) | C + SUV(2) | | 79 |
| anti-DNP | +(3) | — | 6 | |

As seen from the table, buffer alone in the presence of complement produced about 20% non-specific lysis, which was recued to about 16% by including SUV's in the complement. Adding complement alone to REV's containing composition-3 SUV's reduced this non-specific lysis still to about 4% indicating first, that SUV inhibition of complement-related, non-specific lysis does not require preincubating of the complement serum with the SUV's, and secondly, that composition-3 SUV's are more effective than composition-2 SUV's in reducing complement related lysis.

Addition of serum, either in the presence or absence of untreated complement, resulted in about a 75% non-specific lysis level. This level was reduced to about 11% by adding composition-3 SUV's to the mixture containing only human serum, and to about 15%, in the mixture containing both human serum and untreated complement serum. Since untreated complement, in the absence of SUV's, itself produces about a 20% non-specific lysis level, it is seen that composition-3 SUV's added to the serum also act in reducing complement-related non-specific lysis substantially. The addition of SUV's to both the serum complement and human serum resulted in a slight improvement in non-specific lysis level over that in which only the human serum has been treated to contain SUV's. Levels of DNP-specific lysis are not appreciably affected by the addition of composition-3 SUV's to the sample, as seen in the lower rows in TABLE XVI.

EXAMPLE XVII

Effect of Lipid Vesicle Size and Structure On Serum-Related REV Lysis

Above examples XIII-XVI demonstrate the efficacy of selected-composition SUV's in reducing target-cell lysis in the presence of human serum. The present example is concerned with the relative efficiencies of SUV's, REV's and MLV's in reducing serum-related lysis of target cell REV's. Composition-2 REV's (PE-DNP) were prepared in accordance with Example II to contain 200 mM CF. Composition-3 SUV's and MLV's were prepared in accordance with Example II. Composition-3 REV's were prepared as described in Example I, with the exception that the buffer initially added to the lipid solution contained no CF. Human serum, obtained from healthy donors, was stored for 8 days at refrigerator temperature, then diluted 1:10 with assay buffer.

The effect of the different vesicle types on non-specific lysis was tested by mixing 25 microliters of diluted human serum with 32 microliters of buffer or 32 microliters of one of the three different lipid vesicle preparations, in the nanomolar amounts indicated in TABLE XVII below. After a 10 minute incubation period at room temperature, 50 microliters of composition-2 REV's (containing CF) were added, and the reaction mixture was incubated for 30 minutes at room temperature. At the end of the incubation period, 1 ml of buffer was added and the percent marker release determined as described above. The results of the experiment are shown below.

TABLE XVII

| nmoles vesicles | % marker release | | |
|---|---|---|---|
| | SUV's | MLV's | REV's |
| 0 | (72) | (72) | (72) |
| 20 | 13 | — | — |
| 40 | 3 | 26 | 21 |
| 80 | 3 | 14 | 13 |
| 160 | 2 | 8 | 10 |
| 320 | — | 3 | 5 |

The number in parentheses in the top row of TABLE XVII represents the percent marker release measured in the absence of added vesicles.

The data show that a reduction of non-specific lysis to about 3% or less is achieved by the addition of about 40 nanomoles of SUV's, but requires about 8 times more MLV's or REV's.

EXAMPLE XVIII

The Effect of Different Vesicle Types on Specific And Non-Specific Target-Cell Lysis The above example, indicating that relatively large amounts of MLV's or REV's are required for inhibiting non-specific, serum-related REV lysis raises the question of whether ligand-specific REV lysis would also be inhibited at these high vesicle concentrations. Composition-2 REV's encapsulating 200 mM CF, were prepared as in Example I and SUV's, MLV's and REV's (no CF) were prepared as describe in Example XVII. Human serum, obtained from healthy donors, was stored for 7 days at refrigerator temperature then diluted 1:10 with assay buffer. Goat anti-DNP-BSA was obtained from Miles Laboratories, and was diluted 1:10 with assay buffer.

In each test, 25 microliters of sample—either assay buffer, diluted human serum or diluted anti-DNP—were mixed with 64 microliters of assay buffer alone or assay buffer containing different amounts of composition-3 SUV's, REV's or MLV's, as indicated in the second column from the left in TABLE XVIII. Immediately after mixing the sample and lipid vesicles, 50 microliters of composition-2 CF-containing (1 nanomoles REV's) were added, and the mixture was incubated at room temperature for 10 minutes. 25 microliters of complement (Miles Lab, lot #0051), diluted 1:10 with assay buffer, was added and the assay mixture incubated further for 30 minutes at room temperature. The reaction was terminated by the addition of 1 ml of buffer to each sample and the percent marker release calculated as in Example III. The data for non-specific lysis and specific lysis (in the presence of anti-DNP) is shown in the two columns at the right in TABLE XVII. As seen, all three types of vesicles, at the indicated nanomolar concentrations, are effective in reducing non-specific lysis more than 10-fold but, at the same vesicle concentrations, have little or no effect on the percent specific lysis.

TABLE XVIII

| sample | vesicles (nmole) | % non-specific lysis | % specific lysis |
|---|---|---|---|
| human serum | buffer | 61 | |
| human serum | SUV (80) | 5 | |
| human serum | REV (640) | 9 | |
| human serum | MLV (640) | 5 | |
| x-DNP—BSA | buffer | | 68 |
| x-DNP—BSA | SUV (80) | | 68 |
| x-DNP—BSA | REV (640) | | 66 |
| x-DNP—BSA | MLV (640) | | 59 |

The data also support the data from Example XVI showing that lipid vesicles added to human serum, in an amount which effectively inhibits non-specific serum-related lysis, also effectively inhibits non-specific lysis by added serum complement which itself has not been pretreated by the addition of lipid vesicles.

While several embodiments of and examples illustrating or supporting the present invention have been described, it will be obvious to those skilled in the art that various changes and modifications may be made without departing from the invention.

What is claimed is:

1. A homogeneous liposome immunoassay system comprising liposomes having surface-bonded ligand molecules and encapsulated reporter molecules which are detactable upon cell lysis, serum complement, anti-ligand molecules capable of reacting specifically and with high affinity with said ligand molecules in the presence of said complement, to induce ligand-specific cell lysis and release of the encapsulated reporter molecules, and lipid vesicles effective to increase the ratio of ligand-specific lysis to nonspecific lysis produced in the absence of said anti-ligand, where said vesicles are present in an amount which increases said specific to nonspecific ratio more than 2-fold over that achievable in the system in the absence of said vesicles, where both the liposomes and lipid vesicles contain phosphatidylcholine as a major component.

2. The system of claim 1, for use in detecting an anti-ligand analyte in a fluid sample, wherein the anti-ligand molecules are supplied by addition of the fluid sample to the liposomes and the serum complement.

3. The system of claim 1, for use in detecting an analyte which is effective in competing with the surface-bound molecules for binding to the anti-ligand, wherein the system further includes a fluid sample containing the analyte.

4. In a homogeneous liposome immunoassay method in which a suspension of liposomes containing surface-bound ligand molecules and encapsulated reporter molecules is reacted with serum complement and anti-ligand molecules, producing both ligand-specific complement-mediated liposome lysis which is related to the concentration of anti-ligand molecules in the reaction mixture, and nonspecific liposome lysis which is independent of the concentration of anti-ligand molecules, wherein the improvement comprises enhancing the sensitivity and reproducibility of the immunoassay by adding to the serum complement, an amount of lipid vesicles which, when the vesicle-containing complement is reacted with said liposomes and anti-ligand molecules, is effective to increase the ratio of specific to nonspecific complement-mediate liposome lysis at least about 2-fold over that achievable in the absence of the added vesicles, where both the liposomes and lipid vesicles contain phosphatidyl choline as a major lipid component.

5. A homogeneous liposomes immunoassay system comprising liposomes having surface-bound ligand molecules and encapsulated reporter molecules which are detectable upon cell lysis, serum complement, anti-ligand molecules capable of reacting specifically and with high affinity with said ligand molecules in the presence of said complement, to induce ligand-specific cell lysis and release of the encapsulated reporter molecules, and lipid vesicles effective to increase the ratio of ligand-specific lysis to nonspecific lysis produced in the absence of said anti-ligand, where said vesicles are present in an amount which increases said specific to nonspecific ratio more than 2-fold over that achievable in the system in the absence of said vesicles, where both the liposomes and lipid vesicles contain phosphatidylethanolamine or a phosphatidylethanolamine derivative.

6. The system of claim 5, wherein the phosphatidylethanolamine or phosphatidylethanolamine derivative has the form:

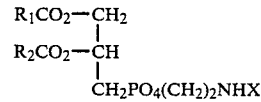

where $R_1$ and $R_2$ are saturated or unsaturated hydrocarbon chains, and $X=H$, $CO_2H$, N-4-(p-moleimidophenyl) butyryl or a hapten against which said anti-ligand molecules are immunospecifically reactive.

7. The system of claim 6, wherein the lipid includes N-4(P-malimidophenyl) butyryl phosphatidylethanolamine.

8. In a homogeneous liposome immunoassay method in which a suspension of liposomes containing surface-bound ligand molecules and encapsulated reporter molecules is reacted with serum complement and anti-ligand molecules, producing both ligand-specific complement-mediated liposome lysis which is related to the concentration of anti-ligand molecules in the reaction mixture, and nonspecific liposome lysis which is independent of the concentration of anti-ligand molecules, wherein the improvement comprises enhancing the sensitivity and reproducibility of the immunoassay by adding to the serum complement, an amount of lipid vesicles which, when the vesicle-containing complement is reacted with said liposomes and anti-ligand molecules, is effective to increase the ratio of specific to nonspecific complement-mediated liposome lysis at least about 2-fold over the achievable in the absence of the added vesicles, where both the liposomes and lipid vesicles contain phosphatidylethanolamine or a derivative thereof.

9. The method of claim 8, wherein the phosphatidyl ethanolamine or derivative includes lipids of the form:

$$\begin{array}{l} R_1CO_2-CH_2 \\ R_2CO_2-CH \\ \phantom{R_2CO_2-}CH_2PO_4(CH_2)_2NHX \end{array}$$

where $R_1$ and $R_2$ are saturated or unsaturated hydrocarbon chains, and X=H, $C_2H$ N-4-(p-maleimidophenyl) butyryl or a hapten against which such-anti-ligand is immunospecifically reactive.

10. The method of claim 9, wherein the lipid vesicles include an N-4-(p-maleimidophenyl) butyryl phosphatidyl ethanolamine.

11. In a homogeneous liposomes immunoassay method in which a suspension of liposomes containing surface-bound ligand molecules and encapsulated reporter molecules is reacted with serum complement and anti-ligand molecules, producing both ligand-specific complement-mediated liposome lysis which is related to the concentration of anti-ligand molecules in the reaction mixture, and nonspecific liposome lysis which is independent of the concentration of anti-ligand molecules, wherein the improvement comprises enhancing the sensitivity and reproducibility of the immunoassay, where the anti-ligand molecules are analyte molecules contained in a serum or plasma sample, by adding to the serum complement, an amount of lipid vesicles which, when the vesicle-containing complement is reacted with said liposomes and said sample containing the anti-ligand molecules, is effective to increase the ratio of specific to nonspecific complement-mediated liposomes lysis at least about 2-fold over the achievable in the absence of the added vesicles.

* * * * *